(12) United States Patent
Weiner et al.

(10) Patent No.: US 7,981,844 B2
(45) Date of Patent: Jul. 19, 2011

(54) METHODS FOR THE MANUFACTURE OF PURE SINGLE ENANTIOMER COMPOUNDS AND FOR SELECTING ENANTIOSELECTIVE ENZYMES

(75) Inventors: David Weiner, Del Mar, CA (US); Tim Hitchman, San Diego, CA (US); Lishan Zhao, Carlsbad, CA (US); Mark J. Burk, San Diego, CA (US); Grace Desantis, San Diego, CA (US); Sarah Richardson Hanson, San Diego, CA (US); Aileen Milan, San Diego, CA (US); Toby Richardson, San Diego, CA (US); Patti Kretz, San Marcos, CA (US); William Greenberg, San Diego, CA (US)

(73) Assignee: Verenium Corporation, San Diego, CA (US)

( * ) Notice: Subject to any disclaimer, the term of this patent is extended or adjusted under 35 U.S.C. 154(b) by 1068 days.

(21) Appl. No.: 10/178,938

(22) Filed: Jun. 21, 2002

(65) Prior Publication Data

US 2003/0092033 A1    May 15, 2003

Related U.S. Application Data

(60) Provisional application No. 60/300,189, filed on Jun. 21, 2001, provisional application No. 60/340,291, filed on Dec. 14, 2001.

(51) Int. Cl.
*C40B 30/08* (2006.01)
*C12P 21/06* (2006.01)
*C12N 9/00* (2006.01)

(52) U.S. Cl. .................. 506/11; 435/69.1; 435/183
(58) Field of Classification Search .............. 506/11; 435/69.1, 183
See application file for complete search history.

(56) References Cited

U.S. PATENT DOCUMENTS

| | | | |
|---|---|---|---|
| 5,128,255 A * | 7/1992 | Crespi | 435/454 |
| 5,759,825 A * | 6/1998 | Wong | 435/136 |
| 5,914,245 A | 6/1999 | Bylina et al. | |
| 5,939,250 A * | 8/1999 | Short | 435/4 |
| 6,017,765 A * | 1/2000 | Yamada et al. | 623/1.15 |
| 6,043,093 A * | 3/2000 | Wohlstadter | 435/6 |
| 6,083,763 A * | 7/2000 | Balch | 506/9 |
| 6,277,588 B1 | 8/2001 | Freeman et al. | |
| 6,368,793 B1 * | 4/2002 | Hoch et al. | 435/6 |
| 6,632,600 B1 * | 10/2003 | Short | 435/4 |

FOREIGN PATENT DOCUMENTS

| | | |
|---|---|---|
| WO | WO 00/22170 | 4/2000 |
| WO | WO 0138583 * | 5/2001 |
| WO | WO0229079 | 4/2002 |

OTHER PUBLICATIONS

Reetz et al., "Enantioselective Enzymes for Organic Synthesis Created by Directed Evolution", Feb. 4, 2000, Chem. Eur. J., 6(3): 407-412.*
Fong et al., "Directed evolution of D-2-keto-3-deoxy-6-phosphogluconate aldolase to new variants for the efficient synthesis of D- and L-sugars", Sep. 22, 2000, Chem. & Biol., 7(11):873-883.*
Fong, et al., "Directed evolution of D-2-keto-3-deoxy-6-phosphogluconate aldolase to new variants for the efficient synthesis of D- and L-sugars", *Chemistry & Biology*, vol. 7, No. 11, pp. 873-883, Nov. 2000.
Jaeger, et al., "Directed evolution of enantioselective enzymes for organic chemistry", *Current Opinion in Chemical Biology*, vol. 4, No. 1, pp. 68-73, Feb. 2000.
Fotheringham et al., J Bacteriol (1998) 180:4319-4323.
Office Action for Canadian Patent Application No. 2,450,577, mailed on Nov. 4, 2008, 4 pages.
EPO—May 10, 2010—94(3) Communication—EP02746619.2.
Reetz—Chemical Communications (2002)—7—1428-1429.

* cited by examiner

*Primary Examiner* — Sue Liu

(57) ABSTRACT

The invention provides biocatalytic methods for the manufacture of pure single enantiomer compounds. This invention provides methods of screening for enzymes which are highly enantioselective or enzymes that can provide any desired stereoisomer of a compound. The invention provides the use of single enantiomer substrates in performing a growth screen of a clonal library to identify highly stereoselective enzymes. In one aspect, methods for screening and identification of enzymes, e.g., transaminases, nitrilases, aldolases, epoxide hydrolases are provided. Methods for the production and screening of gene libraries generated from nucleic acids isolated from more than one organism for enzyme, e.g., transaminase, activities are also provided.

75 Claims, 16 Drawing Sheets

Supply specific enantiomer of
desired product (and acceptor)

Amino acid
growth source

Figure 5
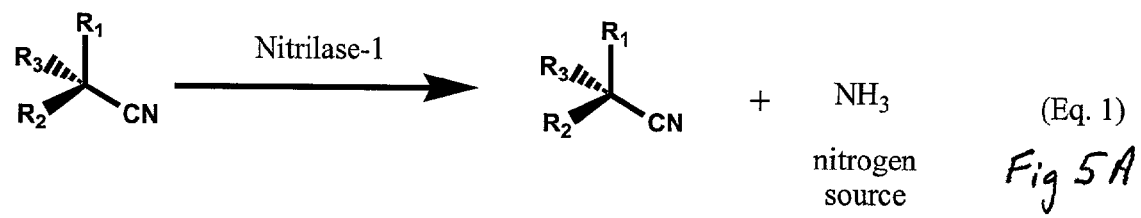
Fig 5A
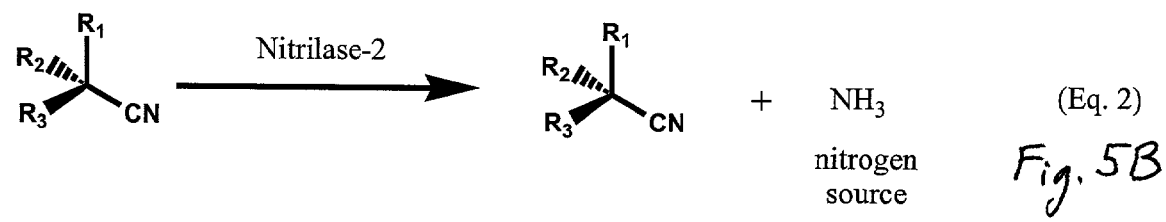
Fig. 5B

METHODS FOR THE MANUFACTURE OF PURE SINGLE ENANTIOMER COMPOUNDS AND FOR SELECTING ENANTIOSELECTIVE ENZYMES

RELATED APPLICATIONS

This application claims the benefit of priority under 35 U.S.C. §119(e) of U.S. Provisional Application Nos. 60/300, 189, filed Jun. 21, 2001, and 60/340,291, filed Dec. 14, 2001. Each of the aforementioned applications are explicitly incorporated herein by reference in their entirety and for all purposes.

TECHNICAL FIELD

This invention relates generally to biochemistry and to the screening and identification of enzymes. In particular, biocatalytic methods for the manufacture of pure single enantiomer compounds. In one aspect, methods for screening and identification of enzymes, e.g., transaminases, nitrilases, aldolases, epoxide hydrolases, are provided. Methods for the production and screening of gene libraries generated from nucleic acids isolated from more than one organism for enzyme, e.g., transaminases, nitrilases, aldolases, epoxide hydrolases, activities are also provided. In one aspect, gene libraries generated from nucleic acids isolated from more than one organism are screened for desired enzymes, e.g., enantiomer selective enzymes, e.g., nitrilases or transaminases activity. Methods for isolating and producing these enzymes are also provided.

BACKGROUND

In order to develop biocatalytic methods for the manufacture of pure single enantiomer compounds, effective procedures must be found to discover enzymes that are highly enantioselective and also enzymes that can provide any desired stereoisomer of a given chiral compound. Identification of highly stereoselective enzymes from a large clonal library is a very challenging task.

Transaminases have been used for the synthesis of natural amino acids for some time. More recently attention has turned to the use of transaminases for the synthesis of chiral unnatural amino acids and chiral amines as illustrated in FIGS. 1A and 1B. Transaminases are a group of key enzymes in the metabolism of amino acids and amino sugars and are found in all organisms from microbes to mammals. In the transamination reaction, an amino group is transferred from an amino acid to an alpha-keto acid. Pyridoxal phosphate is frequently required as a co-factor to mediate the transfer of the amino group without liberation of ammonia. Two important types of organic chiral precursors are chiral unnatural amino acids and chiral amines. Chiral unnatural amino acids and chiral amines can be conveniently produced through catalysis of transaminases as illustrated herein.

There are several attractive features of transaminases that make them promising catalysts for large-scale production of chiral amino acids and amines. These include: (1) No cofactor regeneration is required. Transaminases do not require nicotinamide cofactors. Instead the cofactor (pyridoxal phosphate) is tightly bound to the enzyme. (2) Transaminases are generally highly enantioselective.

One of the main limitations to the widespread application of transaminases is the lack of available enzymes. For example, the current enzymes accept only a limited number of substrates and often suffer from product inhibition. Transaminase reactions are reversible and the equilibrium constant is generally near unity. This can be a challenge in obtaining high yields of products.

Transaminase-catalyzed syntheses of chiral amines and amino acids can be limited by the equilibrium of the reaction which is generally close to unity. Several approaches to driving the equilibrium in the direction of product formation have been described. For example, (1) Addition of molar excesses of amino donors; (2) Removal of alpha-keto acid product either enzymatically or chemically, (3) If the value of the target amine is high enough, it may not be necessary to drive the equilibrium to completion.

There is a need in the chemical industry for efficient catalysts for the practical synthesis of optically pure materials. Enzymes can provide the optimal solution. All classes of molecules and compounds that are utilized in both established and emerging chemical, pharmaceutical, textile, food, animal feed, and detergent markets must meet stringent economical and environmental standards. The synthesis of polymers, pharmaceuticals, natural products and agrochemicals is often hampered by expensive processes, which produce harmful byproducts and which suffer from low enantioselectivity.

Enzymes have a number of remarkable advantages, which can overcome these problems in catalysis: they act on single functional groups, they distinguish between similar functional groups on a single molecule, and they distinguish between enantiomers. Moreover, they are biodegradable and function at very low concentrations in reaction mixtures. Because of their chemo-, regio- and stereospecificity, enzymes present a unique opportunity to optimally achieve desired selective transformations. These are often extremely difficult to duplicate chemically, especially in single-step reactions. The elimination of the need for protection groups, the selectivity of enzymes, the ability to carry out multi-step transformations in a single reaction vessel, along with the concomitant reduction in environmental burden, has led to the increased demand for enzymes in chemical and pharmaceutical industries. Enzyme-based processes have been gradually replacing many conventional chemical-based methods. A current limitation to more widespread industrial use is primarily due to the relatively small number of commercially available enzymes.

The use of enzymes for technological applications may require performance under demanding industrial conditions. This includes activities in environments or on substrates for which the currently known arsenal of enzymes was not evolutionarily selected. Enzymes have evolved by selective pressure to perform very specific biological functions within the milieu of a living organism, under conditions of mild temperature, pH and salt concentration. For the most part, the non-DNA modifying enzyme activities thus far described have been isolated from mesophilic organisms, which represent a very small fraction of the available phylogenetic diversity. The dynamic field of biocatalysis takes on a new dimension with the help of enzymes isolated from microorganisms that thrive in extreme environments. Enzymes obtained from these extremophilic organisms open a new field in biocatalysis.

Transaminases have been known in the literature for many years. Briefly, a transaminase reaction requires two substrates, an amino compound (amino donor) and a keto compound (amino acceptor). The transaminase catalyzes the exchange of the keto group from the keto compound and the amino group from the amino compound. This exchange generates a new amino compound from the keto compound and a new keto compound from the amino compound. Typically only one of the products is desired, generally the new amino compound, and the other is an unwanted by-product. Used in isolation, the enzyme converts the two substrates to the two products. Theoretically, because the reaction is reversible, it proceeds until it reaches equilibrium.

U.S. Pat. No. 4,518,692 ("Rozzell I") discloses a method for producing L-amino acids by reacting L-aspartic acid and various 2-keto acids with transaminases. The Rozzell I method uses L-aspartic acid as the amino acid to produce oxaloacetate and describes various methods of decarboxylating oxaloacetate to form pyruvate. However, the pyruvate produced in the Rozzell I method can still act as a keto donor in the reverse process to form alanine. Tokarski et al., Biotechnology Letters, Vol. 10 (1) (1988), pp. 7-10, show that alanine acts as a substrate in transaminase reactions. See also, Transaminases (1985); and Amino Acids: Biosynthesis and Genetic Regulation, Klaus M. Herrmann and Ronald L. Somerville ed. (1983) (Addison-Wesley Publishing, Reading Mass.). Tokarski, et al. studied the use of a transaminase to produce L-2-aminobutyrate from 2-ketobutyrate and alanine. The reference, however, discloses only 25-30% conversion to products, demonstrating that the reverse reaction is very significant. This has long been considered an intrinsic property and a problem of transaminase reactions and is the major reason such enzyme catalyzed reactions have not been more often exploited in industrial processes to produce these highly desired amine products.

U.S. Pat. No. 4,826,766 ("Rozzell II") discloses an improved transaminase catalyzed reaction that employs two transaminase enzymes and additional keto acids. In the process, a first transaminase enzyme catalyzes the reaction between a first amino acid and a first keto acid to produce a second amino acid and second keto acid. A second transaminase enzyme then catalyzes a further reaction of the second amino acid and a third keto acid to form the desired amino acid. The two transaminase enzymes are selected such that the first enzyme does not catalyze the second reaction and the second enzyme does not catalyze the first reaction.

Another transaminase process, which combines the transaminase enzyme with a second enzyme that eliminates the keto acid produced by the transaminase reaction, preventing the attainment of equilibrium, and driving the amino acid producing reaction to completion, is known from U.S. Pat. No. 6,197,558 (Fotheringham). The second enzyme catalyzes a reaction, which converts the keto acid to a substance that can no longer react with the transaminase. By removing the second keto acid, the second enzyme allows the amino acid producing reaction to proceed to an extent that the desired amino acid product represents approximately 100% of the amino acids produced.

Aldolases are ubiquitous enzymes that catalyze the formation of carbon-carbon bonds through the aldol reaction (FIG. 7). Depending on the donors and acceptors utilized, the reaction generates one or two new stereocenters (indicated by the asterixes in FIG. 1). Thus, aldolases have great potential for the production of advanced chiral products that are difficult and/or expensive to produce by traditional chemical routes. FIG. 8 illustrates a few well-characterized examples of reactions catalyzed by aldolases. In regard to substrate specificity, the aldehyde acceptor component can be varied to some extent (FIG. 3), and the enolate donor requirement is typically quite strict. Some examples of aldolase-mediated synthesis with non-natural substrates have been reported, although these cases are currently limited (see, e.g., JOC 2000, 95, 8264; b. JACS 1996, 118, 2117; c. JACS 1997, 119, 11734). Realization of the synthetic potential of aldolases in large scale industrial processes has been limited by the lack of available enzymes with the necessary properties.

There are two major routes from a nitrile to an analogous acid: (1) a nitrilase catalyzes the direct hydrolysis of a nitrile to a carboxylic acid with the concomitant release of ammonia; or (2) a nitrile hydratase adds a molecule of water across the carbon-nitrogen bonding system to give the corresponding amide, which then acts as a substrate for an amidase enzyme which hydrolyzes the carbon-nitrogen bond to give the carboxylic acid product with the concomitant release of ammonia. The nitrilase enzyme therefore provides the more direct route to the acid.

A nitrile group offers many advantages in devising synthetic routes in that it is often easily introduced into a molecular structure and can be carried through many processes as a masked acid or amide group. This is only of use, however, if the nitrile can be unmasked at the relevant step in the synthesis. Cyanide represents a widely applicable $C_1$-synthon (cyanide is one of the few water-stable carbanions) which can be employed for the synthesis of a carbon framework. However, further transformations of the nitrile thus obtained are impeded due to the harsh reaction conditions required for its hydrolysis using normal chemical synthesis procedures. The use of enzymes to catalyze the reactions of nitrites is attractive because nitrilase enzymes are able to effect reactions with fewer environmentally hazardous reagents and by-products than in many traditional chemical methods. Indeed, the chemoselective biocatalytic hydrolysis of nitrites represents a valuable alternative because it occurs at ambient temperature and near physiological pH.

The importance of asymmetric organic synthesis in drug design and discovery has fueled the search for new synthetic methods and chiral precursors which can be utilized in developing complex molecules of biological interest. One important class of chiral molecules are the α-substituted carboxylic acids, which include the α-amino acids. These molecules have long been recognized as important chiral precursors to a wide variety of complex biologically active molecules, and a great deal of research effort has been dedicated to the development of methods for the synthesis of enantiomerically pure α-amino acids and chiral medicines.

Of particular use to synthetic chemists who make chiral medicines would be an enzyme system which is useful under non-sterile conditions, which is useful in non-biological laboratories, which is available in a form convenient for storage and use; which has broad substrate specificity, which acts on poorly water soluble substrates; which has predictable product structure; which provides a choice of acid or amide product; and which is capable of chiral differentiation. Accordingly, there is a need for efficient, inexpensive, high-yield synthetic methods for producing enantiomerically pure α-substituted carboxylic acids, such as, for example, α-amino acids and α-hydroxy acids.

Chiral epoxides and diols are key building blocks for the synthesis of pharmaceuticals. The epoxide group is readily transformed into a wide range of derivatives by acid or base-catalyzed ring opening reactions, while the diols similarly can be converted into a diverse range of structures. Currently available methods for the enantioselective preparation of chiral epoxides and diols have drawbacks that limit their use in industrial applications. Epoxide hydrolases (E.C. 3.3.2.x) are attractive as biocatalysts for the preparation of chiral epoxides and vicinal diol as they can selectively hydrolyze one of the enantiomers. The selective hydrolysis of a racemic epoxide thus generates both the corresponding diols and the unreacted epoxides with high enantiomeric excess (ee) values.

SUMMARY

The invention provides a versatile method for the discovery of a multitude of enzymes with unique substrate specificities and enantioselectivities. In one aspect, the present invention provides methods comprising performing a growth selection screen on clonal libraries using single enantiomer substrates to discover enzymes with a specific stereoselectivity profile. In this aspect, only clones that can transform a given enantiomer of a substrate to products will grow to form a colony. Any class or type of enantioselective enzyme can be identified using the methods of the invention, e.g., transaminases, nitrilases, aldolases, hydrolases, e.g., epoxide hydrolases, glycosidases, proteases, and other enzymes such as topoisomerases, nucleases, polymerases, amidases, secondary amidases, alpha-galactosidases, alpha-glucosidase, transaminases/aminotransferases, phytases, polymerases, xylanases, amylases, laccases, phospholipases, nitrile hydratases, proteases, lipases, isomerases, monooxygenases, catalases, carboxymethyl cellulases, endoglucanases, glycosidases, esterases, phosphatases, nitroreductases, pectate lyases, oxidoreductases, transferases, lyases, isomerases, ligases, and combinations thereof, to name just a few.

The invention provides a method of screening for and identification of enzymes which are highly enantioselective. The methods are useful for the discovery, identification and isolation of enzymes that are highly enantioselective, as well as for the discovery of enzymes which can provide any desired stereoisomer of a given chiral compound. In another aspect, the invention provides a method for the identification of enzymes which can provide any desired stereoisomer from a given chiral compound.

The invention provides a method for selecting a nucleic acid encoding an enantioselective enzyme comprising the following steps: (a) providing a nucleic acid encoding a polypeptide; (b) providing a plurality of cells, wherein the cells cannot make a factor or element essential for growth and the essential factor or element must be of a specific chirality to induce growth of the cell; (c) providing a precursor or substrate of a specific chirality, a mixed chirality or non-chiral substrate, wherein the precursor or substrate is capable of being converted by an enzyme to an essential factor or element of the same, opposite or mixed chirality or to a non-chiral essential factor or element; (d) inserting the nucleic acid into the cells and growing the cells under conditions wherein the nucleic acid is expressed and its encoded polypeptide is translated, and the cells are grown in a medium lacking the factor or element essential for growth, and adding the substrate of step (c); and, (e) screening the cells for growth, wherein the nucleic acid in the growth stimulated clone is identified as encoding an enantioselective enzyme capable of converting the chiral substrate to a product comprising the chiral essential factor or element and this essential factor or element product of the enzyme's reaction is a single enantiomer, thereby selecting a nucleic acid encoding an enantioselective enzyme.

The invention provides a method for identifying a nucleic acid encoding an enantioselective enzyme comprising the following steps: (a) providing a nucleic acid library; (b) providing a precursor or substrate of a specific chirality, a mixed chirality or non-chiral substrate, wherein the substrate is capable of being converted by an enzyme to an essential factor or element of the same, opposite or mixed chirality or to a non-chiral essential factor or element for a composition essential for growth and to be growth-stimulating the composition essential for growth; (c) providing a plurality of cells, wherein the cells cannot make the composition essential for growth; (d) inserting in a cell a member of the gene library and culturing the cells in a medium lacking the composition essential for growth; (e) adding the precursor of step (b) to the culture; (f) selecting a growing cell and identifying the inserted library member of step (d), wherein the cell is capable of growth by enzymatic conversion of the precursor to a product comprising the composition essential for growth, and the enzyme is encoded by the library member, thereby identifying a nucleic acid encoding an enantioselective enzyme.

The invention provides a method for selecting a nucleic acid encoding an enantioselective enzyme comprising the following steps: (a) providing a nucleic acid encoding a polypeptide; (b) providing a plurality of cells, wherein the cells cannot make a factor or element essential for growth and the essential factor or element must be of a specific chirality to induce growth of the cell; (c) providing a substrate of a specific chirality, wherein the substrate is capable of being converted to an essential factor or element of the same chirality by an enzyme; (d) inserting the nucleic acid into the cells and growing the cells under conditions wherein the nucleic acid is expressed and its encoded polypeptide is translated, and the cells are grown in a medium lacking the factor or element essential for growth, and adding the substrate of step (c); and, (e) screening the cells for growth, wherein the nucleic acid in the growth stimulated clone is identified as encoding an enantioselective enzyme capable of converting the chiral substrate to a product comprising the chiral essential factor or element and this essential factor or element product of the enzyme's reaction is a single enantiomer, thereby selecting a nucleic acid encoding an enantioselective enzyme. The substrate can be added at any point, e.g., it can be included in the media or it can be added after the cells have been cultured. Alternatively, the substrate can be endogenous to the cells, i.e., the cells can be capable of synthesizing the substrate.

All of the reactions of the invention, whether cell-based or in vitro, can take place entirely or partly in an array, e.g., a double-orificed capillary array, such as a GIGAMATRIX™ capillary array.

The invention provides a method for identifying a nucleic acid encoding an enantioselective enzyme comprising the following steps: (a) providing a nucleic acid library; (b) providing a precursor of a specific chirality for a composition essential for growth, wherein the precursor is capable of being enzymatically converted to a product comprising the composition essential for growth, and to be growth-stimulating the composition essential for growth must have a chirality corresponding to the chirality of the precursor; (c) providing a plurality of cells, wherein the cells cannot make the composition essential for growth; (d) inserting in a cell a member of the gene library and culturing the cells in a medium lacking the composition essential for growth; (e) adding the precursor of step (b) to the culture; (f) selecting a growing cell and identifying the inserted library member of step (d), wherein the cell is capable of growth by enzymatic conversion of the precursor to a product comprising the composition essential for growth, and the enzyme is encoded by the library member, thereby identifying a nucleic acid encoding an enantioselective enzyme. The precursor can be added to the cells or medium at any point. Alternatively, the precursor can be endogenously produced by the cells.

The invention provides a growth selection screen using single enantiomer substrates to discover enzymes with a specific stereoselectivity profile comprising the following steps: (a) providing a nucleic acid or a polypeptide library; (b) providing a single enantiomer substrate for a composition essential for growth, wherein the substrate is capable of being converted to a product comprising a composition essential for growth, and to be growth-stimulating the composition essential for growth must have a chirality corresponding to the chirality of the precursor; (c) providing a plurality of cells, wherein the cells cannot make the composition essential for growth; (d) inserting in the cells a member of the nucleic acid or polypeptide library and culturing the cells in a medium lacking the composition essential for growth; (e) adding the single enantiomer substrate of step (b) to the culture; and (f) selecting a growing cell and identifying the inserted nucleic acid or polypeptide of step (d), wherein the cell is capable of growth by enzymatic conversion of the single enantiomer substrate to a product comprising the composition essential for growth, thereby identifying an enzyme with a specific stereoselectivity profile.

In one aspect, the nucleic acid is a member of a nucleic acid or gene library, e.g., a DNA or cDNA library. The library can be obtained from a pure culture or a mixed population of organisms. The mixed population of organisms can be derived from an environmental sample, e.g., a soil sample, a water sample or an air sample.

The methods of the invention can identify a coding sequence for an enzyme with a specific stereoselectivity profile or a polypeptide with a specific stereoselectivity profile for any and all enzymes, e.g., a transaminase, a nitrilase, an aldolase or a hydrolase, e.g., an epoxide hydrolase, a protease, a lipase and the like.

In practicing the invention, the equilibrium of the reaction can be manipulated by any means, e.g., adding substrate/precursor or removing reaction product or both. For example, if a reaction is in equilibrium, a product can be removed to drive reaction toward the product side and/or a substrate can be removed to drive the reaction to substrate side. In one aspect, the equilibrium of the conversion of the substrate or precursor to the product is shifted in the direction of product formation by addition of an excess of substrate or precursor. Alternatively, the equilibrium of the conversion of the product to the substrate or precursor is shifted in the direction of substrate or precursor formation by addition of an excess of product.

In one aspect, the enzyme is a transaminase and the substrate or precursor is a specific enantiomer of an amino acid and the product is a specific enantiomer of an amino donor. The product can further comprises an α-keto acid. The substrate or precursor can comprises a specific enantiomer of an amino donor and the product is a specific enantiomer of an amino acid. The equilibrium of the conversion can be shifted in the direction of amino acid product formation by addition of excess amino donor. The method can further comprise adding an α-keto acid amino acceptor to the media. The equilibrium of the conversion of the product to the substrate or precursor can be shifted in the direction of product formation by enzymatic removal of an α-keto acid product. The equilibrium of the conversion of the specific enantiomer to the specific growth source can shifted in the direction of product formation by chemical removal of α-keto acid product.

In one aspect, the enzyme is a nitrilase, and by supplying only nitrile groups of a desired chirality enantioselective nitrilase enzymes are identified. The substrate or precursor can comprise a specific enantiomer of a nitrile-containing compound and the product comprises a specific enantiomer of a corresponding carboxylic acid and ammonia. The substrate or precursor can comprise a specific enantiomer of a carboxylic acid and the product comprises a specific enantiomer of a nitrile-containing compound. The medium can comprise a nitrogen-free minimal media for cell growth, thereby only clones that can hydrolyze a nitrile group will produce the nitrogen source required to grow.

In one aspect, the enzyme is an aldolase and deoxyribose-5-phosphate comprises the substrate or precursor and acetaldehyde comprises a product of the reaction. The product can further comprise a glyceraldehyde-3-phosphate. The enzyme can be an aldolase and a deoxyribose, a 5-O-methyl-deoxyribose, or a dideoxyribose can comprise the substrate or precursor and an acetaldehyde can comprise a product of the reaction. The precursor or substrate can comprise a deoxyribose and the product can further comprise a glyceraldehyde. The precursor or substrate can comprise a 5-O-methyl-deoxyribose and the product can further comprise a 3-O-methyl-deoxyribose. The precursor or substrate can comprise a dideoxyribose and the product can further comprise a lactaldehyde.

In one aspect, the nucleic acid further comprises an expression cassette, an expression vector, a phage or a plasmid. The vector can be a PAC, a BAC, a MAC or a YAC. The nucleic acid library can comprise phagemid library cells.

In one aspect, the medium comprises a solid substrate or a liquid media.

In one aspect, the cells that cannot make a factor, element or composition essential for growth are auxotrophs. The auxotrophs can amino acid auxotrophs. The auxotrophs can be made by any knockout strategy, e.g., a transposon mutagenesis strategy.

In one aspect, inserting the nucleic acid into a cell comprises infecting, transducing, transforming, infecting or transfecting the cells with the nucleic acid.

Any cells can be used in practicing the methods of the invention. In one aspect, the cells comprise bacterial cells. The bacterial cells comprise *E. coli*, Streptomyces, or *Bacillus subtilis*. The cells can also comprise fungal cells, e.g., Aspergillus. The cells comprise insect cells, such as Drosophila S2 or Spodoptera Sf9. The cells can comprise animal cells, such as CHO cells, a COS cells or a Bowes melanoma cell. The cells can comprise plant cells.

The invention provides a method for identifying an enantioselective enzyme comprising the following steps: (a) providing a polypeptide; (b) providing a plurality of cells, wherein the cells cannot make a factor or element essential for growth and the essential factor or element must be of a specific chirality to induce growth of the cell; (c) providing a substrate of a specific chirality, wherein the substrate is capable of being converted to an essential factor or element of the same chirality by an enzyme; (d) inserting the polypeptide into the cells and culturing the cells, and the cells are grown in a medium lacking the factor or element essential for growth; and, (e) screening the cells for growth, wherein the polypeptide in the growth stimulated clone is identified as being an enantioselective enzyme capable of converting the chiral substrate to a product comprising the chiral essential factor or element and this essential factor or element product of the enzyme's reaction is a single enantiomer, thereby identifying an enantioselective enzyme.

The invention provides a method for identifying an enantioselective enzyme comprising the following steps: (a) providing a polypeptide library; (b) providing a precursor of a specific chirality for a composition essential for growth, wherein the precursor is capable of being enzymatically converted to a product comprising the composition essential for growth, and to be growth-stimulating the composition essential for growth must have a chirality corresponding to the chirality of the precursor; (c) providing a plurality of cells, wherein the cells cannot make the composition essential for growth; (d) inserting in a cell a member of the polypeptide library and culturing the cells in a medium lacking the composition essential for growth; (e) adding the precursor of step (b) to the culture; and (f) selecting a growing cell and identifying the inserted polypeptide of step (d), wherein the cell is capable of growth by enzymatic conversion of the precursor to a product comprising the composition essential for growth, thereby identifying an enantioselective enzyme.

In one aspect, the library is obtained from a mixed population of organisms. The mixed population of organisms can be derived from a soil sample, a water sample or an air sample. The enzyme can be any enzyme, e.g., a transaminase, a nitrilase, an aldolase or an epoxide hydrolase. In one aspect, the reaction mixture comprises a crude, partially purified, or purified enzyme.

In one aspect, the methods further comprise immobilizing the cells. The immobilization can comprise entrapment in arrays, e.g., capillary arrays, e.g., a double-orificed capillary array, e.g., a GIGAMATRIX™ capillary array, polymeric gels, covalent attachment, crosslinking, adsorption or encapsulation. In one aspect, the methods further comprise preparing cell extracts, which can be immobilized. The immobilization can comprise entrapment in arrays, e.g., capillary arrays, e.g., a double-orificed capillary array, e.g., a GIGAMATRIX™ capillary array, polymeric gels, covalent attachment, crosslinking, adsorption or encapsulation.

The invention provides an in vitro growth selection screen using single enantiomer substrates to discover nucleic acids encoding enzymes with specific stereoselectivity profiles that produce a single chiral reaction product comprising the following steps: (a) providing a nucleic acid library; (b) providing a single enantiomer substrate, wherein the substrate is capable of being converted to a product having a chirality corresponding to the chirality of the precursor; (c) providing an in vitro transcription/translation system lacking the enzyme's chiral reaction product; (d) adding to the in vitro transcription/translation system a member of the nucleic acid library; (e) adding the single enantiomer substrate of step (b); and (f) selecting a sample producing the enzyme's chiral reaction product and identifying the inserted nucleic acid of step (d), wherein selecting the sample comprising the enzyme's chiral reaction product selects a nucleic acid encoding an enzyme with a specific stereoselectivity profile.

The invention provides an in vitro growth selection screen using single enantiomer substrates to discover enzymes with specific stereoselectivity profiles that produce a single chiral reaction product comprising the following steps: (a) providing a polypeptide library; (b) providing a single enantiomer substrate, wherein the substrate is capable of being converted to a product having a chirality corresponding to the chirality of the precursor; (c) providing an in vitro transcription/ translation system lacking the enzyme's chiral reaction product; (d) adding to the in vitro transcription/ translation system a member of the polypeptide library; (e) adding the single enantiomer substrate of step (b); and (f) selecting a sample producing the enzyme's chiral reaction product and identifying the added polypeptide of step (d), wherein selecting the sample comprising the enzyme's chiral reaction product selects an enzyme with a specific stereoselectivity profile.

In one aspect, the polypeptide comprises a crude, partially purified, or purified enzyme. The method can further comprise immobilizing the polypeptide or the nucleic acid. The enzymatic reaction of the methods of the invention can take place on a substrate surface. The enzymatic reaction of the methods of the invention can take place in a capillary tube. The enzymatic reaction can take place in a double-orificed capillary array, e.g., a GIGAMATRIX™ capillary array.

The present invention provides rapid screening of samples for bioactivities or biomolecules of interest. Samples can be derived from a wide range of sources and include, for example, environmental libraries, samples containing more than one organisms (e.g., mixed populations of organisms), samples from unculturable organisms, deep sea vents and the like. As described herein, such samples provide a rich source of untapped molecules useful in biologics, therapeutics and industrial application, which prior to the present invention required laborious and time consuming methods for characterization and identification or were unable to be identified or characterized.

In one aspect, the invention provides a method for obtaining a bioactivity or a biomolecule of interest by screening a library of clones generated from nucleic acids from a mixed population of cells, for a specified bioactivity or biomolecule, variegating a nucleic acid sequence contained in a clone having the specified bioactivity or biomolecule; and comparing the variegated bioactivity or biomolecule with the specified bioactivity or biomolecule wherein a difference in the bioactivity or biomolecule is indicative of an effect of sequence variegation, thereby providing the bioactivity or biomolecule of interest.

In another aspect, the invention provides a method for identifying a bioactivity or a biomolecule of interest by screening a library of clones generated from pooled nucleic acids obtained from a plurality of isolates for a specified bioactivity or biomolecule; and identifying a clone which contains the specified bioactivity or biomolecule.

In yet another aspect, the invention provides a method for identifying a bioactivity or a biomolecule of interest. The method includes screening a library of clones generated from pooled nucleic acids obtained from a plurality of isolates for a specified bioactivity or biomolecule, variegating a nucleic acid sequence contained in a clone having the specified bioactivity or biomolecule, and comparing the variegated bioactivity or biomolecule with the specified bioactivity or biomolecule wherein a difference in the bioactivity or biomolecule is indicative of an effect of introducing at least one sequence variegation, thereby providing the bioactivity or biomolecule of interest.

In another aspect, the invention provides a method for identifying a bioactivity or a biomolecule of interest, wherein the method includes screening a library of clones generated from pooling individual gene libraries generated from the nucleic acids obtained from each of a plurality of isolates for a specified bioactivity or biomolecule and identifying a clone which contains the specified bioactivity or biomolecule.

In another aspect, the invention provides a method for identifying a bioactivity or a biomolecule of interest by screening a library for a specified bioactivity or biomolecule wherein the library is generated from pooling individual gene libraries generated from the nucleic acids obtained from each of a plurality of isolates, variegating a nucleic acid sequence contained in a clone having the specified bioactivity or biomolecule, and comparing the variegated bioactivity or biomolecule with the specified bioactivity or biomolecule wherein a difference in the bioactivity or biomolecule is indicative of an effect of introducing at least one sequence variegation, thereby providing the bioactivity or biomolecule of interest.

In one aspect, the invention provides a method of identifying a bioactivity or biomolecule of interest, including screening a library of clones generated from the nucleic acids from an enriched population of organisms for a specified bioactivity or biomolecule and identifying a clone containing the specified bioactivity or biomolecule.

In one aspect, the invention provides a method of identifying a bioactivity or biomolecule of interest by screening a library of clones generated from nucleic acids from an enriched population of organisms for a specified bioactivity or biomolecule, variegating a nucleic acid sequence contained in a clone having the specified bioactivity or biomolecule, and comparing the variegated bioactivity or biomolecule with the specified bioactivity or biomolecule wherein a difference in the bioactivity or biomolecule is indicative of an effect of introducing at least one sequence variegation, thereby providing the bioactivity or biomolecule of interest.

In one aspect, the invention provides a method for identifying a bioactivity or a biomolecule of interest. The bioactivity or biomolecule of interest is identified by incubating nucleic acids from a mixed population of organisms with at least one oligonucleotide probe having a detectable molecule and at least a portion of a nucleic acid sequence encoding a molecule of interest under conditions to allow interaction of complementary sequences, identifying nucleic acid sequences having a complement to the oligonucleotide probe using an analyzer that detects the detectable molecule. A library is then generated from the identified nucleic acid sequences and the library is screened for a specified bioactivity or biomolecule. Nucleic acid sequence contained in a clone having the specified bioactivity or biomolecule is variegated and the variegated bioactivity or biomolecule compared with the specified bioactivity or biomolecule wherein a difference in the bioactivity or biomolecule is indicative of an effect of introducing at least one sequence variation, thereby providing the bioactivity or biomolecule of interest.

In one aspect, the invention provides a method for identifying a bioactivity or a biomolecule of interest by co-encapsulating in a microenvironment nucleic acids obtained from a mixed population of organisms, with at least one oligonucleotide probe having a detectable molecule and at least a portion of a nucleic acid sequence encoding a molecule of interest under such conditions and for such time as to allow interaction of complementary sequences, identifying encapsulated nucleic acids containing a complement to the oligonucleotide probe encoding the molecule of interest by separating the encapsulated nucleic acids with an analyzer that detects the detectable molecule, generating a library from the separated encapsulated nucleic acids, screening the library for a specified bioactivity or biomolecule, variegating a nucleic acid sequence contained in a clone having the specified bioactivity or biomolecule, and comparing the variegated bioactivity or biomolecule with the specified bioactivity or biomolecule wherein a difference in the bioactivity or biomolecule is indicative of an effect of introducing at least one sequence variation, thereby providing the bioactivity or biomolecule of interest.

In one aspect, the invention provides a method including co-encapsulating in a microenvironment nucleic acids obtained from an isolate of a mixed population of organisms, with at least one oligonucleotide probe having a detectable marker and at least a portion of a polynucleotide sequence encoding a molecule having a bioactivity of interest under conditions and for such time as to allow interaction of complementary sequences, identifying encapsulated nucleic acids containing a complement to the oligonucleotide probe encoding the molecule of interest by separating the encapsulated nucleic acids with an analyzer that detects the detectable marker, generating a library from the separated encapsulated nucleic acids, screening the library for a specified bioactivity or biomolecule, variegating a nucleic acid sequence contained in a clone having the specified bioactivity or biomolecule, and comparing the variegated bioactivity or biomolecule with the specified bioactivity or biomolecule wherein a difference in the bioactivity or biomolecule is indicative of an effect of introducing at least one sequence variation, thereby providing the bioactivity or biomolecule of interest.

In one aspect, the invention provides a method for obtaining a bioactivity or a biomolecule of interest by co-encapsulating in a microenvironment nucleic acids obtained from one or more isolates of a mixed population of organisms, with at least one oligonucleotide probe having a detectable marker and at least a portion of a polynucleotide sequence encoding a molecule having a bioactivity of interest under such conditions and for such time as to allow interaction of complementary sequences, identifying encapsulated nucleic acids containing a complement to the oligonucleotide probe encoding the molecule of interest by separating the encapsulated nucleic acids with an analyzer that detects the detectable marker, generating a library from the separated encapsulated nucleic acids, screening the library for a specified bioactivity or biomolecule, variegating a nucleic acid sequence contained in a clone having the specified bioactivity or biomolecule, and comparing the variegated bioactivity or biomolecule with the specified bioactivity or biomolecule wherein a difference in the bioactivity or biomolecule is indicative of an effect of introducing at least one sequence variation, thereby providing the bioactivity or biomolecule of interest.

In one aspect, the invention provides a method for identifying a bioactivity or a biomolecule of interest. The method includes co-encapsulating in a microenvironment nucleic acids obtained from a mixture of isolates of a mixed population of organisms, with at least one oligonucleotide probe having a detectable marker and at least a portion of a polynucleotide sequence encoding a molecule having a bioactivity of interest under such conditions and for such time as to allow interaction of complementary sequences, identifying encapsulated nucleic acids containing a complement to the oligonucleotide probe encoding the molecule of interest by separating the encapsulated nucleic acids with an analyzer that detects the detectable marker, generating a library from the separated encapsulated nucleic acids, screening the library for a specified bioactivity or biomolecule, variegating the a nucleic acid sequence contained in a clone having the specified bioactivity or biomolecule, and comparing the variegated bioactivity or biomolecule with the specified bioactivity or biomolecule wherein a difference in the bioactivity or biomolecule is indicative of an effect of introducing at least one sequence variation, thereby providing the bioactivity or biomolecule of interest.

All publications, patents, patent applications, Gen Bank sequences and ATCC deposits cited herein are hereby expressly incorporated by reference for all purposes.

The details of one or more aspects of the invention are set forth in the accompanying drawings and the description below. Other features, objects, and advantages of the invention will be apparent from the description and drawings, and from the claims.

DESCRIPTION OF DRAWINGS

FIG. 1 is a schematic illustration of two exemplary methods of the invention.

FIGS. 5A and 5B are illustrations of an exemplary method of the invention, wherein only clones possessing a) an active nitrilase enzyme (Nitrilase-1) that can hydrolyze the nitrile enantiomer will grow (Eq. 1); or, b) an active nitrilase enzyme (Nitrilase-2) that can hydrolyze the nitrile enantiomer opposite of that shown in a) will grow (Eq. 2).

Like reference symbols in the various drawings indicate like elements.

DETAILED DESCRIPTION

The present invention provides methods for making compounds, e.g., amino acids, of a specific chirality, i.e., the product of the method is a single enantiomer. Also provided are methods for selecting enzymes whose reaction products are of a specific chirality, i.e., the product of the enzyme's reaction is a single enantiomer.

The present invention presents methods for discovery and identification of enzymes that are highly enantioselective and enzymes that can provide a desired stereoisomer of a given chiral compound. In one aspect, the methods comprise performing a growth selection screen on a clonal library whereby single enantiomer substrates are used to discover enzymes with a specific stereoselectivity profile.

In one exemplary method of the invention, a growth selection screen is performed on a clonal library to generate a single enantiomer reaction product and to discover enzymes with a specific stereoselectivity profile. For example, the methods provides a selection strategy that uses the reversibility of enzyme-catalyzed reactions to advantage and, in essence, searches for clones that can run a reaction backwards from a desired substrate of a specific chirality, e.g., an amine, to produce a desired growth source, e.g., an amino acid, of a specific chirality.

Figure 1A:
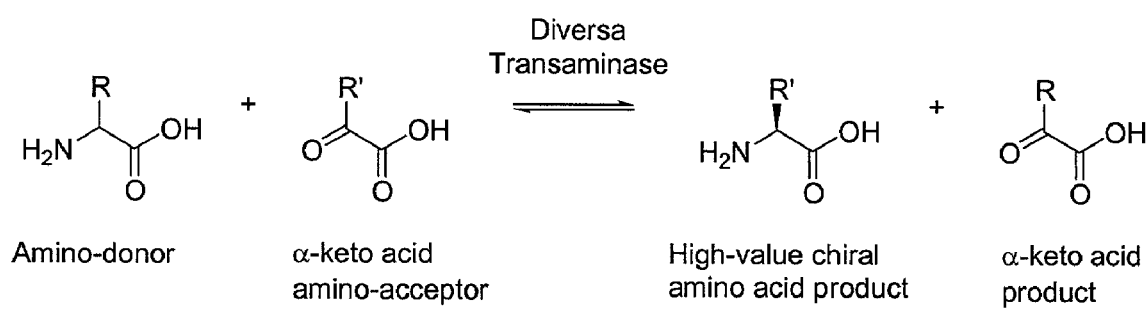
FIG. 1A is an illustration of an exemplary transaminase-catalyzed synthesis of chiral specific amino acids and FIG. 1B is an illustration of an exemplary transaminase-catalyzed synthesis of chiral specific amines.
Figure 1B:
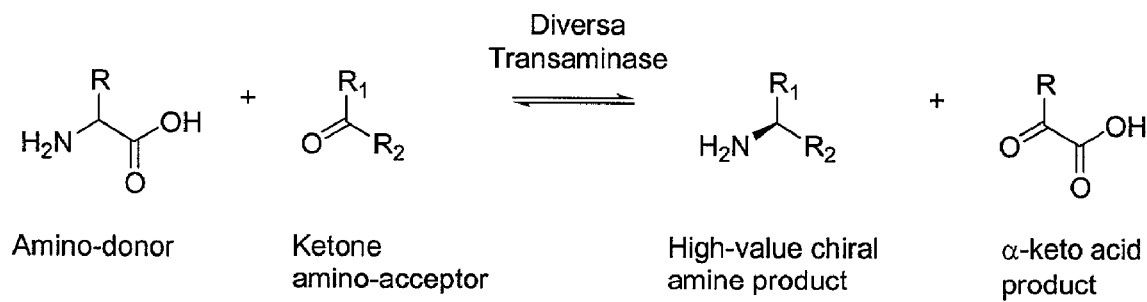
Figure 2:
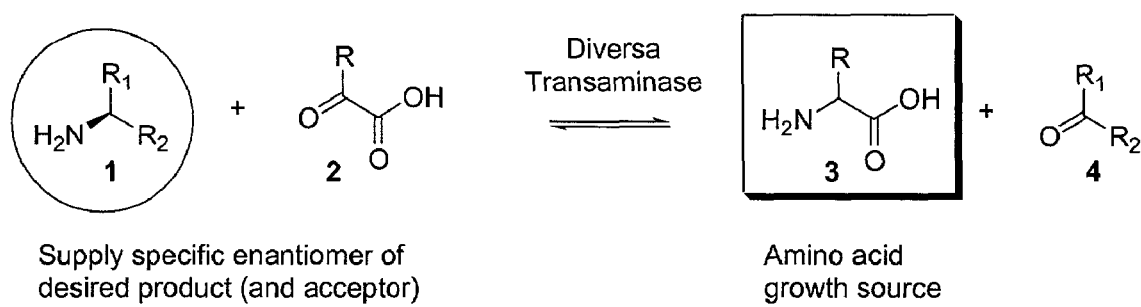
FIG. 2 is a schematic illustration of an exemplary method of the invention, a "reverse" transaminase reaction, which can be used to discover clones capable of synthesizing chiral amines and amino acids.

For example, the invention provides a selection strategy that uses the reversibility of transaminase-catalyzed reactions to advantage and, in essence, searches for clones that can run a reaction backwards from a desired amine to produce a growth source, i.e., a composition essential for growth of the cell, such as an amino acid. The exemplary method comprises:

Phagemid library cells are inoculated into media lacking a crucial growth source 3 (see FIG. 2). Both solid and liquid selections can be used.

Any desired amine (or amino acid) 1 (see FIG. 2) is added to the media. Depending on the natural cellular background levels of the amine acceptor 2 (see FIG. 2), it may or may not be necessary to add exogenous 2.

Only clones harboring an active transaminase that can convert 1 to 3 (see FIG. 2) will grow. See FIGS. 2 and 3. Any host strain can be used. Any desired host strain can be made using routine selection methods. For example, several amino acid auxotrophs (e.g. aspartate or glutamate) can be made via knockout strategies, e.g., transposon mutagenesis.

The selection strategies of the invention are powerful because they offer an extremely high throughput method for screening environmental DNA libraries for enzyme-encoding genes, e.g., transaminase or nitrilases genes. In one aspect, the desired product of a particular biotransformation is used to discover the enzyme for its own synthesis. Thus, the selection is highly specific. Extremely rare biocatalysts are accessible via the methods of the invention. Any chiral amine or amino acid can be used. In one aspect, chiral amines or amino acids that are non-toxic to the cell and are able to permeate the cell membrane are used.

The methods of the invention can use any biocatalytic or metabolic pathway manipulation scheme or methodology, and, the methods of the invention can use any culturing or selection strategy, see, e.g., Hoch, et al., WO 00/22170, U.S. Patent Application Publication Nos. 20020050476; 20020012974; 20020006644.

In another exemplary method, the invention provides growth selection with nitrilases. Nitrilases are a class of enzymes that catalyze the hydrolysis of nitrile-containing compounds into the corresponding carboxylic acid and ammonia. By using nitrogen-free minimal media for growth, only clones that can hydrolyze a nitrile group will produce the nitrogen source required to thrive. In one aspect, by supplying only nitrile groups of a desired chirality, enantioselective enzymes can be identified. By utilizing single enantiomer substrates for the growth selection and identification of enzymes, clones in a library that will rapidly hydrolyze that enantiomer of the substrate can be selected.

In another aspect, opposite enantiomers of a given product can also be selected. By employing the opposite enantiomer of a substrate, only enzymes that can readily hydrolyze the opposite enantiomer will grow. As discussed in Example 1, this exemplary method entails utilizing single enantiomer nitrites. FIG. 5A (Eq. 1) shows that clones possessing an active nitrilase enzyme (Nitrilase-1) that can hydrolyze the nitrile enantiomer shown will grow effectively. By corollary, only clones possessing Nitrilase-2 will survive if provided with the opposite nitrile enantiomer, as shown in FIG. 5B (Eq. 2).

This selection scheme may allow discovery of two different enzymes which may provide either enantiomer of a desired product. The invention also can be applied to other types of nitrites as well as many other classes of enzymes and substrates.

The present invention provides methods of selecting and creating a wide range of transaminases. Transaminase catalyzed reactions are reversible and the equilibrium constant is generally near unity. Even though it is a challenge to obtain high yields of products several methods as described above have been developed to shift the equilibrium towards product formation direction. The method of selecting trans aminases of the present invention utilizes the reversibility of transaminase-catalyzed reactions to its advantage and, in essence, searches for clones that can run a reaction backwards from a desired amine (or amino acid) to produce a growth source. See FIGS. 2 and 3. Once the clones are identified, the desired transaminases may be isolated from the clones.

In one aspect, the method of selecting transaminases according to the present invention includes the steps of:

Inoculating clones containing phagemid library cells into media lacking a crucial growth source 3 of FIG. 2. Both solid and liquid selections can be used.

Adding a particular desired amine or amino acid 1 of FIG. 2 to the media. Depending on the natural cellular background levels of the amine acceptor 2 of FIG. 2, it may or may not be necessary to add exogenous amine acceptor 2 of FIG. 2.

Detecting the clones having substantial cell growths to determine the existence of transaminases because only clones harboring an active transaminase that can convert amine or amino acid 1 to growth source 3 will grow.

In the exemplary method, suitable host strains or cells may be constructed to form the phagemid library cells in the step A) of the method of the present invention. For example, several amino acid auxotrophs (e.g. aspartate or glutamate) can be made via knockout strategies such as transposon mutagenesis or other processes described below.

The processes of the invention are intended to encompass the use of any natural or non-naturally occurring microorganism, such as a bacterium or virus that produces transaminase enzymes. As used herein, the term "non-naturally occurring microorganism" is intended to include all genetically altered microorganisms that produce transaminase enzymes. For example, Rozzell II discloses several microorganism sources for transaminases having selectivities for aromatic amino acids, branched chain amino acids, and amino acids having acidic side chains.

In one aspect of the process, the transaminase enzyme is produced by cells of a non-naturally occurring microorganism that contains a gene encoding a transaminase enzyme. For example, the gene encoding the transaminase can be incorporated into a plasmid that is inserted into a cell such that the cell produces the transaminase enzyme. In another aspect of the invention a multiplicity of transaminase enzymes, for example 2, 3, 4, and the like, can be simultaneously utilized in the process. Thus, as used herein "transaminase enzyme" can comprise one or more than one transaminase enzymes being used simultaneously. In one aspect, whether as a single transaminase enzyme or as one of a multiplicity of transaminase enzymes, the transaminase enzymes used is the enzyme produced by plasmid pME64, as described herein.

Host cells are genetically engineered (transduced or transformed or transfected) with the vectors of this invention, which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

Exemplary appropriate hosts include: bacterial cells, such as E. coli, Streptomyces, *Bacillus subtilis*; fungal cells, such as yeast or Aspergillus; insect cells such as Drosophila S2 and Spodoptera Sf9; animal cells such as CHO, COS or Bowes melanoma; adenoviruses; plant cells; etc. The selection of an appropriate host is deemed to be within the scope of those skilled in the art from the teachings herein.

The process of this invention can be applied to a variety of natural and non-naturally occurring amines and amino acids. In principle, any chiral amine or amino acid may be employed in the step B) of the method as long as it is not toxic to the cell and is able to permeate the cell membrane.

Also, the process of the present invention can be applied to a variety of keto acids. See, e.g., U.S. Pat. No. 4,518,692 and Transaminases, (1985) for disclosures of a broad range of keto acids, which are useful in this invention.

In addition to these sources, keto donors can also be prepared from readily available starting materials, including other amino acids. For example, the enzyme threonine deaminase reacts with L-threonine to produce 2-ketobutyrate. The keto acid, thus produced, is then reacted with the L-aspartate amino acid substrate according to the process described above to produce L-2-aminobutyrate. L-threonine is an inexpensive starting material available from Archer Daniels Midland (Decatur, Ill.). See, Amino Acids: Biosynthesis and Genetic Regulation (1983) cited above.

Additional reactions using various amino acid starting materials to produce various keto acids that are useful in this process are known in the art. Gene, (1989) Vol. 76, pp. 255-269 and Gene, (1988) Vol. 63, pp. 245-252 describe See also, Massad G., et al., J. Bacteriol., (1992) Vol. 177, pp. 5878-5883, for a general description of the activity of amino acid deaminase enzymes from Proteus mirabilis. These references are hereby incorporated in their entireties into this specification.

The method of selecting transaminases of the present invention may be implemented as a high throughput assay for screening environmental DNA libraries for transaminase. Moreover, since the desired product of a particular biotransformation is used to select a transaminase in the method of the invention, which may also catalyze the synthesis of the desired product, the selectivity should be highly specific.

Although transaminase-catalyzed syntheses of chiral amines and amino acids may be limited by the equilibrium of the reaction, which generally has equilibrium constant close to one, several methods to drive the equilibrium in the direction of product formation may be used. These methods of driving the equilibrium include: a) addition of excess amino donors; and b) removal of alpha-keto acid product either enzymatically or chemically. In another aspect, the present invention provides a method of selecting a wide range of transaminases. Transaminase catalyzed reactions are reversible and the equilibrium constant is generally near unity. Even though it is a challenge to obtain high yields of products, several methods are developed to shift the equilibrium towards product formation direction as described in the following sections.

Figure 3:
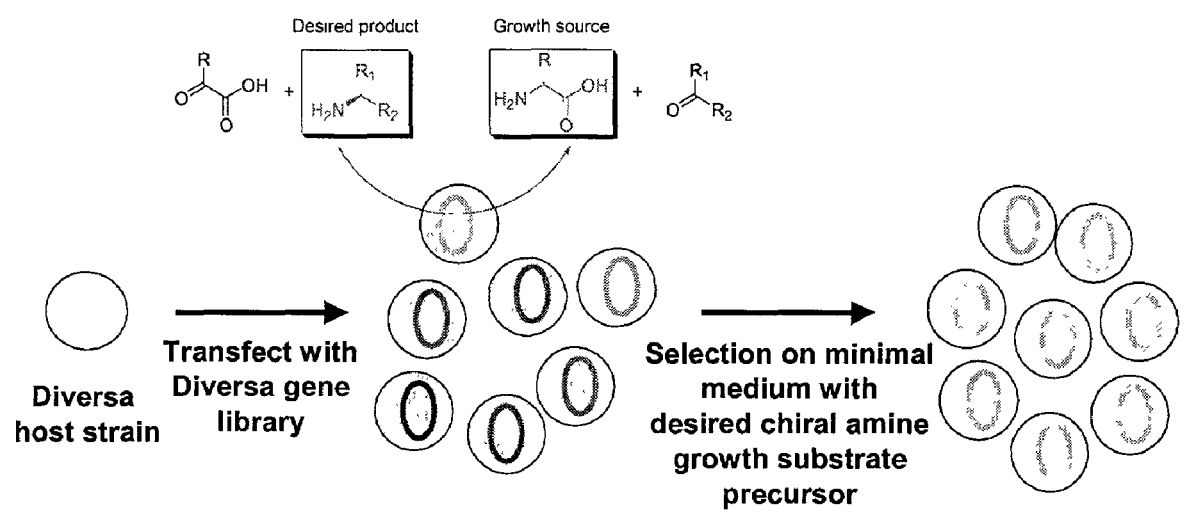
FIG. 3 is a schematic illustration of an exemplary method of the invention, a selection strategy for transaminases.

The method of selecting transaminases of the present invention uses the reversibility of transaminase-catalyzed reactions to its advantage and, in essence, searches for clones that can run a reaction backwards from a desired amine (or amino acid) to produce a growth source (FIGS. 2 and 3). Once the clones are identified, the desired transaminases may be isolated from the clones.

The invention provides a process for producing a keto acid which comprises the step of: a) reacting a first amino acid with a transaminase enzyme selected by the selection method described above under conditions appropriate to produce a keto acid.

Techniques for Utilizing Enzymes

In practicing this invention "conditions appropriate" to react the described enzymes with the described substrates are known to those of ordinary skill in the art. For example, cells producing transaminase enzymes may be contacted with a solution containing the keto acid and amino acid starting materials with the resulting conversion of at least a portion of the keto acid starting material in the reaction mixture to the desired amino acid product. The cells may be permeabilized to facilitate diffusion of the substrates and products into and out of the cells. This permeabilization can be accomplished by treating cells with a low concentration of a surfactant, including but not limited to TWEEN 80, TRITON X-100, NONIDET P40, cetylpyridinium chloride, deoxycholic acid, hexadecyltrimethylammonium bromide or benzalkonium chloride. Further, organic solvents, including but not limited to N,N-dimethylformamide (DMF), dimethyl sulfoxide (DMSO), ethanol or acetone at low concentrations have also been used to increase permeabilization.

Transaminases may also be added to the starting reaction mixture in the form of cell extracts containing crude, partially purified, or purified enzyme. Cell extracts are prepared by methods known to those skilled in the art, which provide for cell disruption and recovery of the enzyme. Cell disruption, can be accomplished by mechanical or non-mechanical means. Most often, for bacterial suspensions mechanical devices such as a French pressure cell, ultrasonication, bead mill or Manton-Gaulin homogenizer is used with the specifics of the method known to those of ordinary skill in the art. See, Scopes, R. K. "Protein Purification", (1982) (Springer-Verlag, New York). The reaction using the cell extract is then carried out in similar fashion to the whole cell method discussed above.

The enzyme-containing cells, or extracts thereof or purified enzyme or enzyme fractions, may also be immobilized, if desired. Immobilization methods, which may be used in the practice of this invention include well-known methods such as entrapment in polymeric gels, covalent attachment, crosslinking, adsorption, and encapsulation. Some examples of these methods are described by A. M. Klibanov in Science, 219:722-727 (1983) and the references therein and in Methods in Enzymology (1976), Volume 44, (K. Mosbach editor) which are hereby incorporated by reference.

In one method of immobilization disclosed in U.S. Pat. No. 5,019,509, a support material containing at least 20% by weight of silica or alumina is contacted with aminoalkyl compound such as an aminoalkyl silane, polyethyleneimine, or a polyalkylamine, followed by activation with glutaraldehyde. The enzyme-containing solution is then contacted with the activated support to produce an immobilized enzyme composition having transaminase- and/or acetolactate synthase activity. Other immobilization supports useful in the practice of this invention include, but are not limited to, porous glass and porous ceramics, bentonite, diatomaceous earth, charcoal SEPHAROSE® and SEPHAROSE® derivatives, cellulose and cellulose derivatives, polyacrylamide and polyacrylamide derivatives, polyazetidine, alginate, carrageenan, and CHROMOSORB®. SEPHAROSE® (Pharmacia Fine Chemicals, Uppsala Sweden) is a bead-formed gel prepared from agarose. The manufacturer's product literature reports that in its natural state, agarose occurs as part of the complex mixture of charged and neutral polysaccharides referred to as agar. The agarose used to make SEPHAROSE® is obtained by a purification process which removes the charged polysaccharides to give a gel with only a very small number of residual charged groups. Those of ordinary skill in the art will appreciate that a number of other materials suitable for the immobilization of cells or extracts derived therefrom may also be useful for the immobilization of the enzymes used in the present invention. These supports can be activated, if desired, by techniques well-known in the art.

The selection process to produce a desired growth source is carried out by contacting a solution containing a first keto acid and a first amino acid with the enzymes under conditions permitting the conversion of at least a portion of the first keto acid to the desired amino acid. In the practice of the processes of this invention the cells contact an aqueous solution of the enzymes at a cell concentration in the range of about 50 mg/ml to about 200 mg/ml. In one aspect the cell concentration is about 100 mg/ml. When the invention is practiced using extracts of cells, the extracts are prepared from an amount of cells that would give these cell concentrations.

The enzymatic reactions of this invention are carried out at temperatures in the range of from about 30° C. to about 50° C., and preferably at temperatures ranging from about 37° C. to about 45° C. The optimal pH for the reaction ranges from about 6 to about 9, and more preferably from about 7 to about 8, with a pH of 8 being most preferred.

The present invention also includes recombinant constructs comprising one or more of the sequences encoding transaminases selected by the selection method of the present invention. The constructs comprise a vector, such as a plasmid or viral vector, into which a sequence of a transaminase selected by the invention has been inserted, in a forward or reverse orientation. In one aspect of this aspect, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS, ptrc99a, pKK223-3, pDR540, pRIT2T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P.sub.R, P.sub.L and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further aspect, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the transaminases can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989).

The present invention provides rapid screening of libraries derived from more than one organism, such as a mixed population of organisms from, for example, an environmental sample or an uncultivated population of organisms or a cultivated population of organisms.

In one aspect, gene libraries are generated by obtaining nucleic acids from a mixed population of organisms and cloning the nucleic acids into a suitable vector for transforming a plurality of clones to generate a gene library. The gene library thus contains gene or gene fragments present in organisms of the mixed population. The gene library can be an expression library, in which case the library can be screened for an expressed polypeptide having a desired activity. Alternatively, the gene library can be screened for sequences of interest by, for example, PCR or hybridization screening.

In one aspect, nucleic acids from isolates of a sample containing a mixed population of organism are pooled and the pooled nucleic acids are used to generate a gene library.

By "isolates" is meant that a particular species, genus, family, order, or class of organisms is obtained or derived from a sample having more than one organism or from a mixed population of organisms. Nucleic acids from these isolated populations can then be used to generate a gene library. Isolates can be obtained from by selectively filtering or culturing a sample containing more than one organism or a mixed population of organisms. For example, isolates of bacteria can be obtained by filtering the sample through a filter which excludes organisms based on size or by culturing the sample on media that allows from selective growth or selective inhibition of certain populations of organisms.

An "enriched population" is a population of organisms wherein the percentage of organisms belonging to a particular species, genus, family, order or class of organisms is increased with respect to the population as a whole. For example, selective growth or inhibition media can increase the overall number of organisms. One can enrich for prokaryotic organisms with respect to the total number of organisms in the population. Similarly, a particular species, genus, family, order or class of organisms can be enriched by growing a mixed population on a selective media that inhibits or promotes the growth of a subpopulation within the mixed population.

In another aspect, nucleic acids from a plurality (e.g., two or more) of isolates from a mixed population of organisms are used to generate a plurality of gene libraries containing a plurality of clones, and the gene libraries from at least two isolates are then pooled to obtain a "pooled isolate library."

Once gene libraries are generated, the clones are screened to detect a bioactivity (e.g., an enzymatic activity, secondary messenger activity, binding activity, transcriptional activity and the like) or a biomolecule of interest (e.g., a nucleic acid sequence, a peptide, a polypeptide, a lipid or other small molecule, and the like). Such screening techniques include, for example, contacting a clone, clonal population, or population of nucleic acid sequences with a substrate or substrates having a detectable molecule that provides a detectable signal upon interaction with the bioactivity or biomolecule of interest. The substrate can be an enzymatic substrate, a bioactive molecule, an oligonucleotide, and the like.

In one aspect, gene libraries are generated, clones are either exposed to a chromagenic or fluorogenic substrate or substrate(s) of interest, or hybridized to a labeled probe (e.g., an oligonucleotide having a detectable molecule) having a sequence corresponding to a sequence of interest and positive clones are identified by a detectable signal (e.g., fluorescence emission).

In one aspect, expression libraries generated from a mixed population of organisms are screened for an activity of interest, such as by the process for screening for transaminase activity that is described above. Specifically, expression libraries are generated, clones are exposed to the substrate or substrate(s) of interest, and positive clone are identified and isolated. The present invention does not require cells to survive. The cells only need to be viable long enough to produce the molecule to be detected, and can thereafter be either viable or nonviable cells, so long as the expressed biomolecule (e.g., an enzyme) remains active.

In certain aspects, the invention provides an approach that combines direct cloning of genes encoding novel or desired bioactivities from environmental samples with a high-throughput screening system designed for the rapid discovery of new molecules, for example, enzymes. The approach is based on the construction of environmental "expression libraries" which can represent the collective genomes of numerous naturally occurring microorganisms archived in cloning vectors that can be propagated in $E.\ coli$ or other suitable host cells. Because the cloned DNA can be initially extracted directly from environmental samples or from isolates of the environmental samples, the libraries are not limited to the small fraction of prokaryotes that can be grown in pure culture. Additionally, a normalization of the environmental DNA present in these samples could allow a more equal representation of the DNA from all of the species present in a sample. Normalization techniques (described below) can dramatically increase the efficiency of finding interesting genes from minor constituents of the sample that may be under-represented by several orders of magnitude compared to the dominant species in the sample. Normalization can occur in any of the foregoing aspects following obtaining nucleic acids from the sample or isolate(s).

In another aspect, the invention provides a high-throughput capillary array system for screening that allows one to assess an enormous number of clones to identify and recover cells encoding useful enzymes, as well as other biomolecules (e.g., ligands). In particular, the capillary array-based techniques described herein can be used to screen, identify and recover proteins having a desired bioactivity or other ligands having a desired binding affinity. For example, binding assays may be conducted by using an appropriate substrate or other marker that emits a detectable signal upon the occurrence of the desired binding event.

In addition, fluorescence activated cell sorting can be used to screen and isolate clones having an activity or sequence of interest. Previously, FACS machines have been employed in the studies focused on the analyses of eukaryotic and prokaryotic cell lines and cell culture processes. FACS has also been utilized to monitor production of foreign proteins in both eukaryotes and prokaryotes to study, for example, differential gene expression, and the like. The detection and counting capabilities of the FACS system have been applied in these examples. However, FACS has never previously been employed in a discovery process to screen for and recover bioactivities in prokaryotes. Furthermore, the present invention does not require cells to survive, as do previously described technologies, since the desired nucleic acid (recombinant clones) can be obtained from alive or dead cells. The cells only need to be viable long enough to produce the compound to be detected, and can thereafter be either viable or non-viable cells so long as the expressed biomolecule remains active. The present invention also solves problems that would have been associated with detection and sorting of E. coli expressing recombinant enzymes, and recovering encoding nucleic acids. Additionally, the present invention includes within its aspects any apparatus capable of detecting fluorescent wavelengths associated with biological material, such apparati are defined herein as fluorescent analyzers (one example of which is a FACS apparatus).

In one aspect, the invention identifies nucleic acid sequences from a mixed population of organisms, isolates, or enriched populations. In this aspect, it is not necessary to express gene products. Nucleic acid sequences of interest can be identified or "biopanned" by contacting a clone, device (e.g. a gene chip), filter, or nucleic acid sample with a probe labeled with a detectable molecule. The probe will typically have a sequence that is substantially identical to the nucleic acid sequence of interest. Alternatively, the probe will be a fragment or full-length nucleic acid sequence encoding a polypeptide of interest. The probe and nucleic acids are incubated under conditions and for such time as to allow the probe and a substantially complementary sequence to hybridize. Hybridization stringency will vary depending on, for example, the length and GC content of the probe. Such factors can be determined empirically (See, for example, Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement)). Once hybridized the complementary sequence can be PCR amplified, identified by hybridization techniques (e.g., exposing the probe and nucleic acid mixture to a film), or detecting the nucleic acid using a chip.

Once a sequence or bioactivity of interest is identified (e.g., an enzyme of interest) the sequence or polynucleotide encoding the bioactivity of interest can be evolved, mutated or derived to modify the amino acid sequence to provide, for example, modified activities such as increased thermostability, specificity or activity.

An "amino acid" is a molecule having the structure wherein a central carbon atom (the α-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

"Protein" or "polypeptide" refers to any polymer of two or more individual amino acids (whether or not naturally occurring) linked via a peptide bond, and occurs when the carboxyl carbon atom of the carboxylic acid group bonded to the α-carbon of one amino acid (or amino acid residue) becomes covalently bound to the amino nitrogen atom of amino group bonded to the α-carbon of an adjacent amino acid. The term "protein" is understood to include the terms "polypeptide" and "peptide" (which, at times may be used interchangeably herein) within its meaning. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also within the scope of the invention and may be referred to herein as "proteins."

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

The term "isolated" or "purified" when referring to a nucleic acid sequence or a polypeptide sequence, respectively, means altered "by the hand of man" from its natural state; i.e., if it occurs in nature, it has been changed or removed from its original environment, or both. For example, a naturally occurring polynucleotide or a polypeptide naturally present in a living animal, a biological sample or an environmental sample in its natural state is not "isolated" or "purified", but the same polynucleotide or polypeptide separated from the coexisting materials of its natural state is "isolated" or "purified", as the term is employed herein. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions).

"Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. A polynucleotide as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term polynucleotide encompasses genomic DNA or RNA (depending upon the organism, i.e., RNA genome of viruses), as well as mRNA encoded by the genomic DNA, and cDNA.

Sources of nucleic acids used to generate a DNA library can be obtained from environmental samples, such as, but not limited to, microbial samples obtained from Arctic and Antarctic ice, water or permafrost sources, materials of volcanic origin, materials from soil or plant sources in tropical areas, droppings from various organisms including mammals and invertebrates, as well as dead and decaying matter and the like. The nucleic acids used to generate the gene libraries can be obtained, for example, from enriched subpopulations or isolates of the sample. In another aspect, DNA of a plurality of isolates can be pooled to create a source of nucleic acids for generation of the library. Alternatively, the nucleic acids can be obtained from a plurality of isolates, a plurality of gene libraries generated from the plurality of isolates to obtain a plurality of gene libraries. Two or more of the gene libraries can be pooled or combined to obtain a pooled isolate library. Thus, for example, nucleic acids may be recovered from either a cultured or non-cultured organism and used to produce an appropriate gene library (e.g., a recombinant expression library) for subsequent determination of the identity of the particular biomolecule of interest (e.g., a polynucleotide sequence) or screened for a bioactivity of interest (e.g., an enzyme or biological activity).

The following outlines a general procedure for producing libraries from both culturable and non-culturable organisms, enriched populations, as well as mixed population of organisms and isolates thereof, which libraries can be probed, sequenced or screened to select therefrom nucleic acid sequences having an identified, desired or predicted biological activity (e.g., an enzymatic activity), which selected nucleic acid sequences can be further evolved, mutagenized or derived.

As used herein, an environmental sample is any sample containing organisms or polynucleotides or a combination thereof Thus, an environmental sample can be obtained from any number of sources (as described above), including, for example, insect feces, hot springs, soil and the like. Any source of nucleic acids in purified or non-purified form can be utilized as starting material. Thus, the nucleic acids may be obtained from any source, which is contaminated by an organism or from any sample containing cells. The environmental sample can be an extract from any bodily sample such as blood, urine, spinal fluid, tissue, vaginal swab, stool, amniotic fluid or buccal mouthwash from any mammalian organism. For non-mammalian (e.g., invertebrates) organisms the sample can be a tissue sample, salivary sample, fecal material or material in the digestive tract of the organism. An environmental sample also includes samples obtained from extreme environments including, for example, hot sulfur pools, volcanic vents, and frozen tundra. The sample can come from a variety of sources. For example, in horticulture and agricultural testing the sample can be a plant, fertilizer, soil, liquid or other horticultural or agricultural product; in food testing the sample can be fresh food or processed food (for example infant formula, seafood, fresh produce and packaged food); and in environmental testing the sample can be liquid, soil, sewage treatment, sludge and any other sample in the environment which is considered or suspected of containing an organism or polynucleotides.

When the sample is a mixture of material containing a mixed population of organisms, for example, blood, soil or sludge, it can be treated with an appropriate reagent which is effective to open the cells and expose or separate the strands of nucleic acids. Although not necessary, this lysing and nucleic acid denaturing step will allow cloning, amplification or sequencing to occur more readily. Further, if desired, the mixed population can be cultured prior to analysis in order to purify or enrich a particular population or a desired isolate (e.g., an isolate of a particular species, genus, or family of organisms) and thus obtaining a purer sample. This is not necessary, however. For example, culturing of organisms in the sample can include culturing the organisms in microdroplets and separating the cultured microdroplets with a cell sorter into individual wells of a multi-well tissue culture plate. Alternatively, the sample can be cultured on any number of selective media compositions designed to inhibit or promote growth of a particular subpopulation of organisms.

Where isolates are derived from the sample containing mixed population of organisms, nucleic acids can be obtained from the isolates as described below. The nucleic acids obtained from the isolates can be used to generate a gene library or, alternatively, be pooled with other isolate fractions of the sample wherein the pooled nucleic acids are used to generate a gene library. The isolates can be cultured prior to extraction of nucleic acids or can be uncultured. Methods of isolating specific populations of organisms present in a mixed population.

Accordingly, the sample comprises nucleic acids from, for example, a diverse and mixed population of organisms (e.g., microorganisms present in the gut of an insect). Nucleic acids are isolated from the sample using any number of methods for DNA and RNA isolation. Such nucleic acid isolation methods are commonly performed in the art. Where the nucleic acid is RNA, the RNA can be reversed transcribed to DNA using primers known in the art. Where the DNA is genomic DNA, the DNA can be sheared using, for example, a 25 gauge needle.

The nucleic acids can be cloned into an appropriate vector. The vector used will depend upon whether the DNA is to be expressed, amplified, sequenced or manipulated in any number of ways known in the art (see, for example, U.S. Pat. No. 6,022,716 which discloses high throughput sequencing vectors). Cloning techniques are known in the art or can be developed by one skilled in the art, without undue experimentation. The choice of a vector will also depend on the size of the polynucleotide sequence and the host cell to be employed in the methods of the invention. Thus, the vector used in the invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are typically used where the specific nucleic acid sequence to be analyzed or modified is large because these vectors are able to stably propagate large polynucleotides.

The vector containing the cloned nucleic acid sequence can then be amplified by plating (i.e., clonal amplification) or transfecting a suitable host cell with the vector (e.g. a phage on an *E. coli* host). The cloned nucleic acid sequence is used to prepare a library for screening (e.g., expression screening, PCR screening, hybridization screening or the like) by transforming a suitable organism. Hosts, known in the art are transformed by artificial introduction of the vectors containing the nucleic acid sequence by inoculation under conditions conducive for such transformation. One could transform with double stranded circular or linear nucleic acid or there may also be instances where one would transform with single stranded circular or linear nucleic acid sequences. By transform or transformation is meant a permanent or transient genetic change induced in a cell following incorporation of new DNA (e.g., DNA exogenous to the cell). Where the cell is a mammalian cell, a permanent genetic change is generally achieved by introduction of the DNA into the genome of the cell. A transformed cell or host cell generally refers to a cell (e.g., prokaryotic or eukaryotic) into which (or into an ancestor of which) has been introduced, by means of recombinant DNA techniques, a DNA molecule not normally present in the host organism.

An exemplary vector for use in the invention contains an f-factor origin replication. The f-factor (or fertility factor) in *E. coli* is a plasmid which effects high frequency transfer of itself during conjugation and less frequent transfer of the bacterial chromosome itself. In a particular aspect cloning vectors referred to as "fosmids" or bacterial artificial chromosome (BAC) vectors are used. These are derived from *E. coli* f-factor which is able to stably integrate large segments of DNA. When integrated with DNA from a mixed uncultured environmental sample, this makes it possible to achieve large genomic fragments in the form of a stable environmental gene library.

The nucleic acids derived from a mixed population or sample may be inserted into the vector by a variety of procedures. In general, the nucleic acid sequence is inserted into an appropriate restriction endonuclease site(s) by procedures known in the art. Such procedures and others are deemed to be within the scope of those skilled in the art. A typical cloning scenario may have DNA "blunted" with an appropriate nuclease (e.g., Mung Bean Nuclease), methylated with, for example, EcoR I Methylase and ligated to EcoR I linkers GGAATTCC (SEQ ID NO:1). The linkers are then digested with an EcoR I Restriction Endonuclease and the DNA size fractionated (e.g., using a sucrose gradient). The resulting size fractionated DNA is then ligated into a suitable vector for sequencing, screening or expression (e.g. a lambda vector and packaged using an in vitro lambda packaging extract).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or $RbCl$ can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be co-transfected with a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). The eukaryotic cell may be a yeast cell (e.g., *Saccharomyces cerevisiae*), an insect cell (e.g., Drosophila sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, or secretion of the gene product should be used. Such host cell lines may include, but are not limited to, CHO, VERO, BHK, HeLa, COS, MDCK, Jurkat, HEK-293, and WI38.

In one aspect, once a library of clones is created using any number of methods, including those described above, the clones are resuspended in a liquid media, for example, a nutrient rich broth or other growth media known in the art. Typically the media is a liquid media, which can be readily pipetted. One or more media types containing at least one clone of the library are then introduced either individually or together as a mixture, into capillaries (all or a portion thereof) in a capillary array.

In another aspect, the library is first biopanned prior to introduction or delivery into a capillary device or other screening techniques. Such biopanning methods enrich the library for sequences or activities of interest. Examples of methods for biopanning or enrichment are described below.

In one aspect, the library can be screened or sorted to enrich for clones containing a sequence or activity of interested based on polynucleotide sequences present in the library or clone. Thus, the invention provides methods and compositions useful in screening organisms for a desired biological activity or biological sequence and to assist in obtaining sequences of interest that can further be used in directed evolution, molecular biology, biotechnological and industrial applications.

After the gene libraries (e.g., an expression library) have been generated one can include the additional step of "biopanning" such libraries prior to expression screening. The "biopanning" procedure refers to a process for identifying clones having a specified biological activity by screening for sequence homology in a library of clones.

The probe sequence used for selectively interacting with the target sequence of interest in the library can be a full-length coding region sequence or a partial coding region sequence for a known bioactivity. The library can be probed using mixtures of probes comprising at least a portion of the sequence encoding a known bioactivity or having a desired bioactivity. These probes or probe libraries can be single-stranded. In one aspect, the library is preferably been converted into single-stranded form. The probes that are particularly suitable are those derived from DNA encoding bioactivities having an activity similar or identical to the specified bioactivity, which is to be screened. The probes can be used to PCR amplify and thus select target sequences. Alternatively, the probe sequences can be used as hybridization probes, which can be used to identify sequences with substantial or a desired homology.

In another aspect, in vivo biopanning may be performed utilizing a FACS-based machine. Gene libraries or expression libraries are constructed with vectors, which contain elements, which stabilize transcribed RNA. For example, the inclusion of sequences which result in secondary structures such as hairpins, which are designed to flank the transcribed regions of the RNA would serve to enhance their stability, thus increasing their half life within the cell. The probe molecules used in the biopanning process consist of oligonucleotides labeled with detectable molecules that provide a detectable signal upon interaction with a target sequence (e.g., only fluoresce upon binding of the probe to a target molecule). Various dyes or stains well known in the art, for example those described in "Practical Flow Cytometry", 1995 Wiley-Liss, Inc., Howard M. Shapiro, M.D., can be used to intercalate or associate with nucleic acid in order to "label" the oligonucleotides. These probes are introduced into the recombinant cells of the library using one of several transformation methods. The probe molecules interact or hybridize to the transcribed target mRNA or DNA resulting in DNA/RNA heteroduplex molecules or DNA/DNA duplex molecules. Binding of the probe to a target will yield a detectable signal (e.g., a fluorescent signal), which is detected and sorted by a FACS machine, or the like, during the screening process.

The probe DNA should be at least about 10 bases, or can be at least 15 bases, or more. In one aspect, an entire coding region of one part of a pathway may be employed as a probe. Where the probe is hybridized to the target DNA in an in vitro system, conditions for the hybridization in which target DNA is selectively isolated by the use of at least one DNA probe will be designed to provide a hybridization stringency of at least about 50% sequence identity, more particularly a stringency providing for a sequence identity of at least about 70%.

Hybridization techniques for probing a microbial DNA library to isolate target DNA of potential interest are well known in the art and any of those which are described in the literature are suitable for use herein including, for example, chip-based assays, membrane-based assays, and the like.

The resultant libraries of transformed clones can then be further screened for clones, which display an activity of interest. Clones can be shuttled in alternative hosts for expression of active compounds, or screened using methods described herein.

An alternative to the in vivo biopanning described above is an encapsulation technique such as, for example, gel microdroplets, which may be employed to localize multiple clones in one location to be screened on a FACS machine. Clones can then be broken out into individual clones to be screened again on a FACS machine to identify positive individual clones. Screening in this manner using a FACS machine is fully described in patent application Ser. No. 08/876,276 filed Jun. 16, 1997. Thus, for example, if a clone mixture has a desirable activity, then the individual clones may be recovered and re-screened utilizing a FACS machine to determine which of such clones has the specified desirable activity.

Different types of encapsulation strategies and compounds or polymers can be used with the present invention. For instance, high temperature agarose can be employed for making microdroplets stable at high temperatures, allowing stable encapsulation of cells subsequent to heat-kill steps utilized to remove all background activities when screening for thermostable bioactivities. Encapsulation can be in beads, high temperature agaroses, gel microdroplets, cells, such as ghost red blood cells or macrophages, liposomes, or any other means of encapsulating and localizing molecules.

For example, methods of preparing liposomes have been described (e.g., U.S. Pat. Nos. 5,653,996, 5,393,530 and 5,651,981), as well as the use of liposomes to encapsulate a variety of molecules (e.g., U.S. Pat. Nos. 5,595,756, 5,605,703, 5,627,159, 5,652,225, 5,567,433, 4,235,871, 5,227,170). Entrapment of proteins, viruses, bacteria and DNA in erythrocytes during endocytosis has been described, as well (see, for example, Journal of Applied Biochemistry 4, 418-435 (1982)). Erythrocytes employed as carriers in vitro or in vivo for substances entrapped during hypo-osmotic lysis or dielectric breakdown of the membrane have also been described (reviewed in Ihler, G. M. (1983) J. Pharm. Ther). These techniques are useful in the present invention to encapsulate samples in a microenvironment for screening.

"Microenvironment," as used herein, is any molecular structure which provides an appropriate environment for facilitating the interactions necessary for the method of the invention. An environment suitable for facilitating molecular interactions includes, for example, liposomes. Liposomes can be prepared from a variety of lipids including phospholipids, glycolipids, steroids, long-chain alkyl esters; e.g., alkyl phosphates, fatty acid esters; e.g., lecithin, fatty amines and the like. A mixture of fatty material may be employed such a combination of neutral steroid, a charge amphiphile and a phospholipid. Illustrative examples of phospholipids include lecithin, sphingomyelin and dipalmitoylphos-phatidylcholine. Representative steroids include cholesterol, cholestanol and lanosterol. Representative charged amphiphilic compounds generally contain from 12-30 carbon atoms. Mono- or dialkyl phosphate esters, or alkyl amines; e.g., dicetyl phosphate, stearyl amine, hexadecyl amine, dilauryl phosphate, and the like.

Further, it is possible to combine some or all of the above aspects such that a normalization step is performed prior to generation of the expression library, the expression library is then generated, the expression library so generated is then biopanned, and the biopanned expression library is then screened using a high throughput cell sorting and screening instrument. Thus there are a variety of options, including: (i) generating the library and then screen it; (ii) normalize the target DNA, generate the library and screen it; (iii) normalize, generate the library, biopan and screen; or (iv) generate, biopan and screen the library. The nucleic acids used to generate a library can be obtained, for example, from environmental samples, mixed populations of organisms (e.g., cultured or uncultured), enriched populations thereof, and isolates thereof. In addition, the screening techniques include, for example, hybridization screening, PCR screening, expression screening, and the like.

Gel microdroplet or other related technologies can be used in the present invention to localize, sort as well as amplify signals in the high throughput screening of recombinant libraries. Cell viability during the screening is not an issue or concern since nucleic acid can be recovered from the microdroplet.

The biopanning approach described above can be used to create libraries enriched with clones carrying sequences homologous to a given probe sequence. Using this approach libraries containing clones with inserts of up to 40 kbp can be enriched approximately 1,000 fold after each round of panning. This enables one to reduce the number of clones to be screened after 1 round of biopanning enrichment. This approach can be applied to create libraries enriched for clones carrying sequence of interest related to a bioactivity of interest for example polyketide sequences.

Hybridization screening using high-density filters or biopanning has proven an efficient approach to detect homologues of pathways containing conserved genes. To discover novel bioactive molecules that may have no known counterparts, however, other approaches are necessary. One approach is to employ the transaminase screening method described above. Another approach of the present invention is to screen in *E. coli* for the expression of small molecule ring structures or "backbones". Because the genes encoding these polycyclic structures can often be expressed in *E. coil* the small molecule backbone can be manufactured albeit in an inactive form. Bioactivity is conferred upon transferring the molecule or pathway to an appropriate host that expresses the requisite glycosylation and methylation genes that can modify or "decorate" the structure to its active form. Thus, inactive ring compounds, recombinantly expressed in *E. coli* are detected to identify clones, which are then shuttled to a metabolically rich host, such as Streptomyces, for subsequent production of the bioactive molecule. The use of high throughput robotic systems allows the screening of hundreds of thousands of clones in multiplexed arrays in microtiter dishes.

One approach to detect and enrich for clones carrying these structures is to use the capillary screening methods or FACS screening, a procedure described and exemplified in U.S. Ser. No. 08/876,276, filed Jun. 16, 1997. Polycyclic ring compounds typically have characteristic fluorescent spectra when excited by ultraviolet light. Thus, clones expressing these structures can be distinguished from background using a sufficiently sensitive detection method. For example, high throughput FACS screening can be utilized to screen for small molecule backbones in *E. coli* libraries. Commercially available FACS machines are capable of screening up to 100,000 clones per second for UV active molecules. These clones can be sorted for further FACS screening or the resident plasmids can be extracted and shuttled to Streptomyces for activity screening.

In an alternate screening approach, after shuttling to Streptomyces hosts, organic extracts from candidate clones can be tested for bioactivity by susceptibility screening against test organisms such as Staphylococcus aureus, E. coli, or Saccharomyces cervisiae. FACS screening can be used in this approach by co-encapsulating clones with the test organism.

An alternative to the above-mentioned screening methods provided by the present invention is an approach termed "mixed extract" screening. The "mixed extract" screening approach takes advantage of the fact that the accessory genes needed to confer activity upon the polycyclic backbones are expressed in metabolically rich hosts, such as Streptomyces, and that the enzymes can be extracted and combined with the backbones extracted from E. coli clones to produce the bioactive compound in vitro. Enzyme extract preparations from metabolically rich hosts, such as Streptomyces strains, at various growth stages are combined with pools of organic extracts from E. coli libraries and then evaluated for bioactivity.

Another approach to detect activity in the E. coli clones is to screen for genes that can convert bioactive compounds to different forms. For example, a recombinant enzyme was recently discovered that can convert the low value daunomycin to the higher value doxorubicin. Similar enzyme pathways are being sought to convert penicillins to cephalosporins.

Capillary screening, for example, can also be used to detect expression of UV fluorescent molecules in metabolically rich hosts, such as Streptomyces. Recombinant oxytetracylin retains its diagnostic red fluorescence when produced heterologously in S. lividans TK24. Pathway clones, which can be identified by the methods and systems of the invention, can thus be screened for polycyclic molecules in a high throughput fashion.

Recombinant bioactive compounds can also be screened in vivo using "two-hybrid" systems, which can detect enhancers and inhibitors of protein-protein or other interactions such as those between transcription factors and their activators, or receptors and their cognate targets. In this aspect, both a small molecule pathway and a GFP reporter construct are co-expressed. Clones altered in GFP expression can then be identified and the clone isolated for characterization.

The present invention also allows for the transfer of cloned pathways derived from uncultivated samples into metabolically rich hosts for heterologous expression and downstream screening for bioactive compounds of interest using a variety of screening approaches briefly described above.

After viable or non-viable cells, each containing a different expression clone from the gene library is screened, and positive clones are recovered, DNA can be isolated from positive clones utilizing techniques well known in the art. The DNA can then be amplified either in vivo or in vitro by utilizing any of the various amplification techniques known in the art. In vivo amplification would include transformation of the clone(s) or subclone(s) into a viable host, followed by growth of the host. In vitro amplification can be performed using techniques such as the polymerase chain reaction. Once amplified the identified sequences can be "evolved" or sequenced.

One advantage afforded by present invention is the ability to manipulate the identified biomolecules or bioactivities to generate and select for encoded variants with altered sequence, activity or specificity.

Clones found to have biomolecules or bioactivities for which the screen was performed can be subjected to directed mutagenesis to develop new biomolecules or bioactivities with desired properties or to develop modified biomolecules or bioactivities with particularly desired properties that are absent or less pronounced in nature (e.g., wild-type activity), such as stability to heat or organic solvents. Any of the known techniques for directed mutagenesis are applicable to the invention. Exemplary mutagenesis techniques for use in accordance with the invention include those described below.

Alternatively, it may be desirable to variegate a biomolecule (e.g., a peptide, protein, or polynucleotide sequence) or a bioactivity (e.g., an enzymatic activity) obtained, identified or cloned as described herein. Such variegation can modify the biomolecule or bioactivity in order to increase or decrease, for example, a polypeptide's activity, specificity, affinity, function, and the like. DNA shuffling can be used to increase variegation in a particular sample. DNA shuffling is meant to indicate recombination between substantially homologous but non-identical sequences, in some aspects DNA shuffling may involve crossover via non-homologous recombination, such as via cer/lox and/or flp/frt systems and the like (see, for example, U.S. Pat. No. 5,939,250, issued to Dr. Jay Short on Aug. 17, 1999, and assigned to Diversa Corporation, the disclosure of which is incorporated herein by reference). Various methods for shuffling, mutating or variegating polynucleotide or polypeptide sequences are discussed below.

Nucleic acid shuffling is a method for in vitro or in vivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides. In contrast to cassette mutagenesis, only shuffling and error-prone PCR allow one to mutate a pool of sequences blindly (without sequence information other than primers).

The template polynucleotide, which may be used in the methods of the invention may be DNA or RNA. It may be of various lengths depending on the size of the gene or shorter or smaller polynucleotide to be recombined or reassembled. Template polynucleotides can be from about 50 bp to 50 kb, or more. It is contemplated that entire vectors containing the nucleic acid encoding the protein of interest can be used in the methods of the invention, and in fact have been successfully used.

The template polynucleotide may be obtained by amplification using the PCR reaction (U.S. Pat. Nos. 4,683,202 and 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of crossover clones.

The template polynucleotide often is double-stranded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double-or single-stranded polynucleotides are subjected to sexual PCR which includes slowing or halting to provide a mixture of from about 5 bp to 5 kb or more. The size of the random polynucleotides can be from about 10 bp to 1000 bp, or, the size of the polynucleotides can be from about 20 bp to 500 bp.

Alternatively, it is also contemplated that double-stranded nucleic acid having multiple nicks may be used in the methods of the invention. A nick is a break in one strand of the double-stranded nucleic acid. The distance between such nicks can be between about 5 bp to 5 kb, or more, or between about 10 bp to 1000 bp. This can provide areas of self-priming to produce shorter or smaller polynucleotides to be included with the polynucleotides resulting from random primers.

The concentration of any one specific polynucleotide will not be greater than 1% by weight of the total polynucleotides, or the concentration of any one specific nucleic acid sequence will not be greater than 0.1% by weight of the total nucleic acid.

The number of different specific polynucleotides in the mixture will be at least about 100, or, at least about 500, or, at least about 1000, or more.

At this step single-stranded or double-stranded polynucleotides, either synthetic or natural, may be added to the random double-stranded shorter or smaller polynucleotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, or the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1:100, or the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

The mixed population of random polynucleotides are denatured to form single-stranded polynucleotides and then re-annealed. Only those single-stranded polynucleotides having regions of homology with other single-stranded polynucleotides will re-anneal.

Heating may be used to denature the random polynucleotides. One skilled in the art could determine the conditions necessary to completely denature the double-stranded nucleic acid. The temperature can be from 80° C. to 100° C., or the temperature is from 90° C. to 96° C. Other methods, which may be used to denature the polynucleotides include pressure and pH.

The polynucleotides may be re-annealed by cooling. In one aspect, the temperature is from 20° C. to 75° C., or the temperature is from 40° C. to 65° C. If a high frequency of crossovers is needed based on an average of only 4 consecutive bases of homology, recombination can be forced by using a low annealing temperature, although the process becomes more difficult. The degree of renaturation, which occurs, will depend on the degree of homology between the populations of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art.

The approach to be used for the assembly depends on the minimum degree of homology that should still yield crossovers. If the areas of identity are large, Taq polymerase can be used with an annealing temperature of between 45-65° C. If the areas of identity are small, Klenow polymerase can be used with an annealing temperature of between 20-30° C. One skilled in the art could vary the temperature of annealing to increase the number of cross-overs achieved.

The polymerase may be added to the random polynucleotides prior to annealing, simultaneously with annealing or after annealing.

The cycle of denaturation, renaturation and incubation in the presence of polymerase is referred to herein as shuffling or reassembly of the nucleic acid. This cycle is repeated for a desired number of times. The cycle can repeated from 2 to 50 times, or more, or the sequence is repeated from 10 to 40 times.

The resulting nucleic acid is a larger double-stranded polynucleotide of from about 50 bp to about 100 kb, or more, or, the larger polynucleotide is from 500 bp to 50 kb.

This larger polynucleotides may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling. These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. Nos. 4,683,195 and 4,683,202), rather than by digestion of the concatamer.

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell.

The resulting bacterial population will include a number of recombinant polynucleotides having random mutations. This mixed population may be tested to identify the desired recombinant polynucleotides. The method of selection will depend on the polynucleotide desired.

For example, if a polynucleotide, identified by the methods of described herein, encodes a protein with a first binding affinity, subsequent mutated (e.g., shuffled) sequences having an increased binding efficiency to a ligand may be desired. In such a case the proteins expressed by each of the portions of the polynucleotides in the population or library may be tested for their ability to bind to the ligand by methods known in the art (i.e. panning, affinity chromatography). If a polynucleotide, which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides, which confer the desired properties onto the protein.

One skilled in the art could use a phage display system in which fragments of the protein are expressed as fusion proteins on the phage surface (Pharmacia, Milwaukee Wis.). The recombinant DNA molecules are cloned into the phage DNA at a site, which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus, the fusion protein, which is partially encoded by the recombinant DNA molecule is displayed on the phage particle for detection and selection by the methods described above.

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type polynucleotides and a sub-population of nucleic acid from the first or subsequent rounds of nucleic acid shuffling in order to remove any silent mutations from the sub-population.

Any source of nucleic acid, in a purified form can be utilized as the starting nucleic acid. Thus the process may employ DNA or RNA including messenger RNA, which DNA or RNA may be single or double stranded. In addition, a DNA-RNA hybrid, which contains one strand of each may be utilized. The nucleic acid sequence may be of various lengths depending on the size of the nucleic acid sequence to be mutated. The specific nucleic acid sequence can be from 50 to 50,000 base pairs, or more. It is contemplated that entire vectors containing the nucleic acid encoding the protein of interest may be used in the methods of the invention.

Any specific nucleic acid sequence can be used to produce the population of hybrids by the present process. It is only necessary that a small population of hybrid sequences of the specific nucleic acid sequence exist or be available for the present process.

A population of specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into *E. coli* and propagated as a pool or library of hybrid plasmids.

Alternatively, a small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once a mixed population of specific nucleic acid sequences is generated, the polynucleotides can be used directly or inserted into an appropriate cloning vector, using techniques well-known in the art.

The choice of vector depends on the size of the polynucleotide sequence and the host cell to be employed in the methods of the invention. The templates of the invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids can be used where the specific nucleic acid sequence to be mutated is larger because these vectors are able to stably propagate large polynucleotides.

If a mixed population of the specific nucleic acid sequence is cloned into a vector it can be clonally amplified. Utility can be readily determined by screening expressed polypeptides.

The DNA shuffling method of the invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle, which are well-known in the art. This shuffling can be used to create scaffold-like proteins with various combinations of mutated sequences for binding.

The equivalents of some standard genetic matings may also be performed by shuffling in vitro. For example, a "molecular backcross" can be performed by repeatedly mixing the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (e.g., immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

It is also contemplated that the method of the invention can be used for the in vitro amplification of a whole genome from a single cell as is needed for a variety of research and diagnostic applications. DNA amplification by PCR typically includes sequences of about 40 kb. Amplification of a whole genome such as that of E. coli (5,000 kb) by PCR would require about 250 primers yielding 125 forty kb polynucleotides. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatamer containing many copies of the genome.

A 100-fold amplification in the copy number and an average polynucleotide size of greater than 50 kb may be obtained when only random polynucleotides are used. It is thought that the larger concatamer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner. Moreover, the invention provides a method of shuffling that is applicable to a wide range of polynucleotide sizes and types, including the step of generating polynucleotide monomers to be used as building blocks in the reassembly of a larger polynucleotide. For example, the building blocks can be fragments of genes or they can be comprised of entire genes or gene pathways, or any combination thereof.

In an aspect of in vivo shuffling, a mixed population of a specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this aspect, specific nucleic acid sequences will be present in vectors, which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

It has been found that when two polynucleotides, which have regions of identity are inserted into the host cells homologous recombination occurs between the two polynucleotides. Such recombination between the two mutated specific nucleic acid sequences will result in the production of double or triple hybrids in some situations.

It has also been found that the frequency of recombination is increased if some of the mutated specific nucleic acid sequences are present on linear nucleic acid molecules. Therefore, in a one aspect, some of the specific nucleic acid sequences are present on linear polynucleotides.

After transformation, the host cell transformants are placed under selection to identify those host cell transformants which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination. In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild-type sequence, such that at least one wild-type nucleic acid sequence and a mutated nucleic acid sequence are present in the same host cell after transformation. Recombination with the wild-type specific nucleic acid sequence will eliminate those neutral mutations that may affect unselected characteristics such as immunogenicity but not the selected characteristics.

In another aspect of the invention, it is contemplated that during the first round a subset of specific nucleic acid sequences can be generated as smaller polynucleotides by slowing or halting their PCR amplification prior to introduction into the host cell. The size of the polynucleotides must be large enough to contain some regions of identity with the other sequences so as to homologously recombine with the other sequences. The size of the polynucleotides will range from 0.03 kb to 100 kb, or, from 0.2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. The reaction conditions suitable for separating the strands of nucleic acid are well known in the art.

The steps of this process can be repeated indefinitely, being limited only by the number of possible hybrids, which can be achieved.

Therefore, the initial pool or population of mutated template nucleic acid is cloned into a vector capable of replicating, in a bacterium such as $E.\ coli$. The particular vector is not essential, so long as it is capable of autonomous replication in $E.\ coli$. In a one aspect, the vector is designed to allow the expression and production of any protein encoded by the mutated specific nucleic acid linked to the vector. The vector can contain a gene encoding for a selectable marker.

The population of vectors containing the pool of mutated nucleic acid sequences is introduced into the $E.\ coli$ host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations, which differ from the original parent mutated sequences. The host cells are then clonally replicated and selected for the marker gene present on the vector. Only those cells having a plasmid will grow under the selection. The host cells, which contain a vector are then tested for the presence of favorable mutations.

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above. This cycle can be repeated a number of times until the nucleic acid or peptide having the desired characteristics is obtained. It is contemplated that in subsequent cycles, the population of mutated sequences, which are added to the hybrids may come from the parental hybrids or any subsequent generation.

In an alternative aspect, the invention provides a method of conducting a "molecular" backcross of the obtained recombinant specific nucleic acid in order to eliminate any neutral mutations. Neutral mutations are those mutations, which do not confer onto the nucleic acid or peptide the desired properties. Such mutations may however confer on the nucleic acid or peptide undesirable characteristics. Accordingly, it is desirable to eliminate such neutral mutations. The method of the invention provides a means of doing so.

In this aspect, after the hybrid nucleic acid, having the desired characteristics, is obtained by the methods of the aspects, the nucleic acid, the vector having the nucleic acid or the host cell containing the vector and nucleic acid is isolated.

The nucleic acid or vector is then introduced into the host cell with a large excess of the wild-type nucleic acid. The nucleic acid of the hybrid and the nucleic acid of the wild-type sequence are allowed to recombine. The resulting recombinants are placed under the same selection as the hybrid nucleic acid. Only those recombinants, which retained the desired characteristics, will be selected. Any silent mutations, which do not provide the desired characteristics, will be lost through recombination with the wild-type DNA. This cycle can be repeated a number of times until all of the silent mutations are eliminated.

In a another aspect, the invention provides for a method for shuffling, assembling, reassembling, recombining, and/or concatenating at least two polynucleotides to form a progeny polynucleotide (e.g., a chimeric progeny polynucleotide that can be expressed to produce a polypeptide or a gene pathway). In a particular aspect, a double stranded polynucleotide (e.g., two single stranded sequences hybridized to each other as hybridization partners) is treated with an exonuclease to liberate nucleotides from one of the two strands, leaving the remaining strand free of its original partner so that, if desired, the remaining strand may be used to achieve hybridization to another partner.

In a particular aspect, a double stranded polynucleotide end (that may be part of—or connected to—a polynucleotide or a non-polynucleotide sequence) is subjected to a source of exonuclease activity. Enzyme with 3' exonuclease activity, an enzyme with 5' exonuclease activity, an enzyme with both 3' exonuclease activity and 5' exonuclease activity, and any combination thereof can be used in the invention. An exonuclease can be used to liberate nucleotides from one or both ends of a linear double stranded polynucleotide, and from one to all ends of a branched polynucleotide having more than two ends.

By contrast, a non-enzymatic step may be used to shuffle, assemble, reassemble, recombine, and/or concatenate polynucleotide building blocks that is comprised of subjecting a working sample to denaturing (or "melting") conditions (for example, by changing temperature, pH, and /or salinity conditions) so as to melt a working set of double stranded polynucleotides into single polynucleotide strands. For shuffling, it is desirable that the single polynucleotide strands participate to some extent in annealment with different hybridization partners (i.e. and not merely revert to exclusive re-annealment between what were former partners before the denaturation step). The presence of the former hybridization partners in the reaction vessel, however, does not preclude, and may sometimes even favor, re-annealment of a single stranded polynucleotide with its former partner, to recreate an original double stranded polynucleotide.

In contrast to this non-enzymatic shuffling step comprised of subjecting double stranded polynucleotide building blocks to denaturation, followed by annealment, the invention further provides an exonuclease-based approach requiring no denaturation—rather, the avoidance of denaturing conditions and the maintenance of double stranded polynucleotide substrates in annealed (i.e. non-denatured) state are necessary conditions for the action of exonucleases (e.g., exonuclease III and red alpha gene product). In further contrast, the generation of single stranded polynucleotide sequences capable of hybridizing to other single stranded polynucleotide sequences is the result of covalent cleavage—and hence sequence destruction—in one of the hybridization partners. For example, an exonuclease III enzyme may be used to enzymatically liberate 3' terminal nucleotides in one hybridization strand (to achieve covalent hydrolysis in that polynucleotide strand); and this favors hybridization of the remaining single strand to a new partner (since its former partner was subjected to covalent cleavage).

It is particularly appreciated that enzymes can be discovered, optimized (e.g., engineered by directed evolution), or both discovered and optimized specifically for the instantly disclosed approach that have more optimal rates and/or more highly specific activities &/or greater lack of unwanted activities. In fact it is expected that the invention may encourage the discovery and/or development of such designer enzymes.

Furthermore, it is appreciated that one can protect the end of a double stranded polynucleotide or render it susceptible to a desired enzymatic action of an exonuclease as necessary. For example, a double stranded polynucleotide end having a 3' overhang is not susceptible to the exonuclease action of exonuclease III. However, it may be rendered susceptible to the exonuclease action of exonuclease III by a variety of means; for example, it may be blunted by treatment with a polymerase, cleaved to provide a blunt end or a 5' overhang, joined (ligated or hybridized) to another double stranded polynucleotide to provide a blunt end or a 5' overhang, hybridized to a single stranded polynucleotide to provide a blunt end or a 5' overhang, or modified by any of a variety of means).

According to one aspect, an exonuclease may be allowed to act on one or on both ends of a linear double stranded polynucleotide and proceed to completion, to near completion, or to partial completion. When the exonuclease action is allowed to go to completion, the result will be that the length of each 5' overhang will be extend far towards the middle region of the polynucleotide in the direction of what might be considered a "rendezvous point" (which may be somewhere near the polynucleotide midpoint). Ultimately, this results in the production of single stranded polynucleotides (that can become dissociated) that are each about half the length of the original double stranded polynucleotide.

Thus, the exonuclease-mediated approach is useful for shuffling, assembling and/or reassembling, recombining, and concatenating polynucleotide building blocks. The polynucleotide building blocks can be up to ten bases long or tens of bases long or hundreds of bases long or thousands of bases long or tens of thousands of bases long or hundreds of thousands of bases long or millions of bases long or even longer.

Subjecting a double stranded polynucleotide to fragmentation may be used to generate substrates for an exonuclease. Fragmentation may be achieved by mechanical means (e.g., shearing, sonication, and the like), by enzymatic means (e.g., using restriction enzymes), and by any combination thereof. Fragments of a larger polynucleotide may also be generated by polymerase-mediated synthesis.

Additional examples of enzymes with exonuclease activity include red-alpha and venom phosphodiesterases. Red alpha (red gene product (also referred to as lambda exonuclease) is of bacteriophage origin. Red alpha gene product acts processively from 5'-phosphorylated termini to liberate mononucleotides from duplex DNA (Takahashi & Kobayashi, 1990). Venom phosphodiesterases (Laskowski, 1980) is capable of rapidly opening supercoiled DNA.

In one aspect, the present invention provides a non-stochastic method termed synthetic ligation reassembly (SLR), that is somewhat related to stochastic shuffling, save that the nucleic acid building blocks are not shuffled or concatenated or chimerized randomly, but rather are assembled non-stochastically.

The SLR method does not depend on the presence of a high level of homology between polynucleotides to be shuffled. The invention can be used to non-stochastically generate libraries (or sets) of progeny molecules comprised of over $10^{100}$ different chimeras. Conceivably, SLR can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating, by design, a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one aspect of the invention, the annealed building pieces are treated with an enzyme, such as a ligase (e.g., T4 DNA ligase) to achieve covalent bonding of the building pieces.

In a another aspect, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. As a representative list of families of enzymes which may be mutagenized in accordance with the aspects of the present invention, there may be mentioned, the following enzymes and their functions: Lipase/Esterase, Protease, Glycosidase/Glycosyl, transferase, Phosphatase/Kinase, Mono/Dioxygenase, Haloperoxidase, Lignin, peroxidase/Diarylpropane peroxidase, Epoxide hydrolase, Nitrile hydratase/nitrilase, Transaminase, Amidase/Acylase. These exemplifications, while illustrating certain specific aspects of the invention, do not portray the limitations or circumscribe the scope of the disclosed invention.

Thus according to one aspect of the invention, the sequences of a plurality of progenitor nucleic acid templates identified using the methods of the invention are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a demarcation point is an area of homology (comprised of at least one homologous nucleotide base)

shared by at least two progenitor templates, but the demarcation point can be an area of homology that is shared by at least half of the progenitor templates, at least two thirds of the progenitor templates, at least three fourths of the progenitor templates, or, at almost all of the progenitor templates. A demarcation point can be an area of homology that is shared by all of the progenitor templates.

In another aspect, the ligation reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the invention, the possibility of unwanted side products is greatly reduced.

In yet another aspect, the invention provides that, the ligation reassembly process is performed systematically, for example in order to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated can comprise a library of finalized chimeric nucleic acid molecules having an overall assembly order that is chosen by design. In one aspect, such a generated library comprises greater than $10^3$ to greater than $10^{1000}$ different progeny molecular species.

In one aspect, a set of finalized chimeric nucleic acid molecules, produced as described is comprised of a polynucleotide encoding a polypeptide. According to one aspect, this polynucleotide is a gene, which may be a man-made gene. According to another aspect, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a demarcation point.

Thus, according to another aspect, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). The artificially introduced intron(s) can be functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In one instance, the recombination is facilitated by, or occurs at, areas of homology between the man-made intron-containing gene and a nucleic acid with serves as a recombination partner. The recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic ligation reassembly method of the invention utilizes a plurality of nucleic acid building blocks, each of which can have two ligatable ends. The two ligatable ends on each nucleic acid building block may be two blunt ends (i.e. each having an overhang of zero nucleotides), or, one blunt end and one overhang, or, two overhangs.

An overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

A nucleic acid building block can be generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Alternative sizes for building block range from 1 base pair (not including any overhangs) to 100,000 base pairs (not including any overhangs). Other size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one aspect, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another aspect, the two strands of a double-stranded nucleic acid building block are complementary at fewer than every nucleotide apart from any that form an overhang. Thus, according to this aspect, a double-stranded nucleic acid building block can be used to introduce codon degeneracy. The codon degeneracy can be introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

The invention provides a method for selecting a subset of polynucleotides from a starting set of polynucleotides, which method is based on the ability to discriminate one or more selectable features (or selection markers) present anywhere in a working polynucleotide, so as to allow one to perform selection for (positive selection) and/or against (negative selection) each selectable polynucleotide. In a one aspect, a method is provided termed end-selection, which method is based on the use of a selection marker located in part or entirely in a terminal region of a selectable polynucleotide, and such a selection marker may be termed an "end-selection marker".

End-selection may be based on detection of naturally occurring sequences or on detection of sequences introduced experimentally (including by any mutagenesis procedure mentioned herein and not mentioned herein) or on both, even within the same polynucleotide. An end-selection marker can be a structural selection marker or a functional selection marker or both a structural and a functional selection marker. An end-selection marker may be comprised of a polynucleotide sequence or of a polypeptide sequence or of any chemical structure or of any biological or biochemical tag, including markers that can be selected using methods based on the detection of radioactivity, of enzymatic activity, of fluorescence, of any optical feature, of a magnetic property (e.g., using magnetic beads), of immunoreactivity, and of hybridization.

End-selection may be applied in combination with any method for performing mutagenesis. Such mutagenesis methods include, but are not limited to, methods described herein (supra and infra). Such methods include, by way of non-limiting exemplification, any method that may be referred herein or by others in the art by any of the following terms: "saturation mutagenesis", "shuffling", "recombination", "re-assembly", "error-prone PCR", "assembly PCR", "sexual PCR", "crossover PCR", "oligonucleotide primer-directed mutagenesis", "recursive (and/or exponential) ensemble mutagenesis (see Arkin and Youvan, 1992)", "cassette mutagenesis", "in vivo mutagenesis", and "in vitro mutagenesis". Moreover, end-selection may be performed on molecules produced by any mutagenesis and/or amplification method (see, e.g., Arnold, 1993; Caldwell and Joyce, 1992; Stemmer, 1994) following which method it is desirable to select for (including to screen for the presence of) desirable progeny molecules.

In addition, end-selection may be applied to a polynucleotide apart from any mutagenesis method. In a one aspect, end-selection, as provided herein, can be used in order to facilitate a cloning step, such as a step of ligation to another polynucleotide (including ligation to a vector). The invention thus provides for end-selection as a means to facilitate library construction, selection and/or enrichment for desirable polynucleotides, and cloning in general.

In a another aspect, end-selection can be based on (positive) selection for a polynucleotide; alternatively end-selection can be based on (negative) selection against a polynucleotide; and alternatively still, end-selection can be based on both (positive) selection for, and on (negative) selection against, a polynucleotide. End-selection, along with other methods of selection and/or screening, can be performed in an iterative fashion, with any combination of like or unlike selection and/or screening methods and mutagenesis or directed evolution methods, all of which can be performed in an iterative fashion and in any order, combination, and permutation. It is also appreciated that end-selection may also be used to select a polynucleotide in a: circular (e.g., a plasmid or any other circular vector or any other polynucleotide that is partly circular), and/or branched, and/or modified or substituted with any chemical group or moiety.

In one non-limiting aspect, end-selection of a linear polynucleotide is performed using a general approach based on the presence of at least one end-selection marker located at or near a polynucleotide end or terminus (that can be either a 5' end or a 3' end). In one particular non-limiting exemplification, end-selection is based on selection for a specific sequence at or near a terminus such as, but not limited to, a sequence recognized by an enzyme that recognizes a polynucleotide sequence. An enzyme that recognizes and catalyzes a chemical modification of a polynucleotide is referred to herein as a polynucleotide-acting enzyme. In one aspect, polynucleotide-acting enzymes are exemplified non-exclusively by enzymes with polynucleotide-cleaving activity, enzymes with polynucleotide-methylating activity, enzymes with polynucleotide-ligating activity, and enzymes with a plurality of distinguishable enzymatic activities (including non-exclusively, e.g., both polynucleotide-cleaving activity and polynucleotide-ligating activity).

It is appreciated that relevant polynucleotide-acting enzymes include any enzymes identifiable by one skilled in the art (e.g., commercially available) or that may be developed in the future, though currently unavailable, that are useful for generating a ligation compatible end, can be a sticky end, in a polynucleotide. It may be preferable to use restriction sites that are not contained, or alternatively that are not expected to be contained, or alternatively that are unlikely to be contained (e.g., when sequence information regarding a working polynucleotide is incomplete) internally in a polynucleotide to be subjected to end-selection. It is recognized that methods (e.g., mutagenesis methods) can be used to remove unwanted internal restriction sites. It is also appreciated that a partial digestion reaction (i.e. a digestion reaction that proceeds to partial completion) can be used to achieve digestion at a recognition site in a terminal region while sparing a susceptible restriction site that occurs internally in a polynucleotide and that is recognized by the same enzyme. In one aspect, partial digest are useful because it is appreciated that certain enzymes show preferential cleavage of the same recognition sequence depending on the location and environment in which the recognition sequence occurs.

It is also appreciated that protection methods can be used to selectively protect specified restriction sites (e.g., internal sites) against unwanted digestion by enzymes that would otherwise cut a working polypeptide in response to the presence of those sites; and that such protection methods include modifications such as methylations and base substitutions (e.g., U instead of T) that inhibit an unwanted enzyme activity.

In another aspect of the invention, a useful end-selection marker is a terminal sequence that is recognized by a polynucleotide-acting enzyme that recognizes a specific polynucleotide sequence. In one aspect of the invention, useful polynucleotide-acting enzymes also include other enzymes in addition to classic type II restriction enzymes. According to this preferred aspect of the invention, useful polynucleotide-acting enzymes also include gyrases (e.g., topoisomerases), helicases, recombinases, relaxases, and any enzymes related thereto.

It is appreciated that, end-selection can be used to distinguish and separate parental template molecules (e.g., to be subjected to mutagenesis) from progeny molecules (e.g., generated by mutagenesis). For example, a first set of primers, lacking in a topoisomerase I recognition site, can be used to modify the terminal regions of the parental molecules (e.g., in polymerase-based amplification). A different second set of primers (e.g., having a topoisomerase I recognition site) can then be used to generate mutated progeny molecules (e.g., using any polynucleotide chimerization method, such as interrupted synthesis, template-switching polymerase-based amplification, or interrupted synthesis; or using saturation mutagenesis; or using any other method for introducing a topoisomerase I recognition site into a mutagenized progeny molecule) from the amplified template molecules. The use of topoisomerase I-based end-selection can then facilitate, not only discernment, but selective topoisomerase I-based ligation of the desired progeny molecules.

It is appreciated that an end-selection approach using topoisomerase-based nicking and ligation has several advantages over previously available selection methods. In sum, this approach allows one to achieve direction cloning (including expression cloning).

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of bio-pharmaceutical drug development and molecular biology is the identification of peptide structures, including the primary amino acid sequences, of peptides or peptidomimetics that interact with biological macromolecules. One method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members), which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publications WO 91/17271, WO 91/18980, WO 91/19818 and WO 93/08278.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific aspect of the invention selected, and can include encapsulation in a phage particle or incorporation in a cell.

One advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The invention also provides a method for shuffling a pool of polynucleotide sequences identified by the methods of the invention and selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s)

is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round(s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one aspect, selected library members are cloned in a prokaryotic vector (e.g., plasmid, phagemid, or bacteriophage) wherein a collection of individual colonies (or plaques) representing discrete library members are produced. Individual selected library members can then be manipulated (e.g., by site-directed mutagenesis, cassette mutagenesis, chemical mutagenesis, PCR mutagenesis, and the like) to generate a collection of library members representing a kernal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand)).

The in vitro and in vivo shuffling methods of the invention are used to recombine CDRs, which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or cDNA) from antibody-producing cells (e.g., plasma cells/splenocytes from an immunized wild-type mouse, a human, or a transgenic mouse capable of making a human antibody as in WO 92/03918, WO 93/12227, and WO 94/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRs) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members which have relatively low affinity, whereas a low density (valency) can preferentially enrich for higher affinity scfv library members.

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members), which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

The invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat (Kabat et al., 1991); the pool (s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some aspects, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1\times10^6$ unique CDR sequences are included in the collection, although occasionally $1\times10^7$ to $1\times10^8$ unique CDR sequences are present, especially if conservative amino acid substitutions are permitted at positions where the conservative amino acid substituent is not present or is rare (i.e., less than 0.1 percent) in that position in naturally—occurring human CDRS. In general, the number of unique CDR sequences included in a library should not exceed the expected number of primary transformants in the library by more than a factor of 10. Such single-chain antibodies generally bind of about at least $1\times10$ m–, preferably with an affinity of about at least $5\times10^7$ M–1, more preferably with an affinity of at least $1\times10^8$ M–1 to $1\times10^9$ M–1 or more, sometimes up to $1\times10^{10}$ M–1 or more. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, L-selectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. For example, scfv have been produced in plants (Firek et al., 1993) and can be readily made in prokaryotic systems (Owens and Young, 1994; Johnson and Bird, 1991). Furthermore, the single-chain antibodies can be used as a basis for constructing whole antibodies or various fragments thereof (Kettleborough et al., 1994). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, 1982). Once purified, partially or to homogeneity as desired, the polypeptides may then be used therapeutically or in developing and performing assay procedures, immunofluorescent stainings, and the like (see, generally, Lefkovits and Pernis, 1979 and 1981; Lefkovits, 1997).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

Shuffling can also be used to recombinatorially diversify a pool of selected library members obtained by screening a two-hybrid screening system to identify library members, which bind a predetermined polypeptide sequence. The selected library members are pooled and shuffled by in vitro and/or in vivo recombination. The shuffled pool can then be screened in a yeast two hybrid system to select library members which bind said predetermined polypeptide sequence (e.g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al., 1991). This approach identifies protein-protein interactions in vivo through reconstitution of a transcriptional activator (Fields and Song, 1989), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacz, HIS3) which is operably linked to a Gal4 binding site. Typically, the two-hybrid method is used to identify novel polypeptide sequences, which interact with a known protein (Silver and Hunt, 1993; Durfee et al., 1993; Yang et al., 1992; Luban et al., 1993; Hardy et al., 1992; Bartel et al., 1993; and Vojtek et al., 1993). However, variations of the two-hybrid method have been used to identify mutations of a known protein that affect its binding to a second known protein (Li and Fields, 1993; Lalo et al., 1993; Jackson et al., 1993; and Madura et al., 1993). Two-hybrid systems have also been used to identify interacting structural domains of two known proteins (Bardwell et al., 1993; Chakrabarty et al., 1992; Staudinger et al., 1993; and Milne and Weaver 1993) or domains responsible for oligomerization of a single protein (Iwabuchi et al., 1993; Bogerd et al., 1993). Variations of two-hybrid systems have been used to study the in vivo activity of a proteolytic enzyme (Dasmahapatra et al., 1992). Alternatively, an *E. coli*/BCCP interactive screening system (Germino et al., 1993; Guarente, 1993) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymerase (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

The invention is further directed to a method for generating a selected mutant polynucleotide sequence (or a population of selected polynucleotide sequences) typically in the form of amplified and/or cloned polynucleotides, whereby the selected polynucleotide sequences(s) possess at least one desired phenotypic characteristic (e.g., encodes a polypeptide, promotes transcription of linked polynucleotides, binds a protein, and the like) which can be selected for. One method for identifying hybrid polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

In one aspect, the present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequences, optimally introducing mutations into said polynucleotides or copies, (2) pooling the polynucleotides or copies, (3) producing smaller or shorter polynucleotides by interrupting a random or particularized priming and synthesis process or an amplification process, and (4) performing amplification, preferably PCR amplification, and optionally mutagenesis to homologously recombine the newly synthesized polynucleotides.

It is an object of the invention to provide a process for producing hybrid polynucleotides, which express a useful hybrid polypeptide by a series of steps comprising:

(a) producing polynucleotides by interrupting a polynucleotide amplification or synthesis process with a means for blocking or interrupting the amplification or synthesis process and thus providing a plurality of smaller or shorter polynucleotides due to the replication of the polynucleotide being in various stages of completion;

(b) adding to the resultant population of single- or double-stranded polynucleotides one or more single- or double-stranded oligonucleotides, wherein said added oligonucleotides comprise an area of identity in an area of heterology to one or more of the single- or double-stranded polynucleotides of the population;

(c) denaturing the resulting single- or double-stranded oligonucleotides to produce a mixture of single-stranded polynucleotides, optionally separating the shorter or smaller polynucleotides into pools of polynucleotides having various lengths and further optionally subjecting said polynucleotides to a PCR procedure to amplify one or more oligonucleotides comprised by at least one of said polynucleotide pools;

(d) incubating a plurality of said polynucleotides or at least one pool of said polynucleotides with a polymerase under conditions which result in annealing of said single-stranded polynucleotides at regions of identity between the single-stranded polynucleotides and thus forming of a mutagenized double-stranded polynucleotide chain;

(e) optionally repeating steps (c) and (d);

(f) expressing at least one hybrid polypeptide from said polynucleotide chain, or chains; and (g) screening said at least one hybrid polypeptide for a useful activity.

In a one aspect of the invention, the means for blocking or interrupting the amplification or synthesis process is by utilization of UV light, DNA adducts, DNA binding proteins.

In one aspect of the invention, the DNA adducts, or polynucleotides comprising the DNA adducts, are removed from the polynucleotides or polynucleotide pool, such as by a process including heating the solution comprising the DNA fragments prior to further processing.

In another aspect, clones, which are identified as having a biomolecule or bioactivity of interest, may also be sequenced to identify the DNA sequence encoding a polypeptide (e.g., an enzyme) or the polypeptide sequence itself having the specified activity, for example. Thus, in accordance with the present invention it is possible to isolate and identify: (i) DNA encoding a bioactivity of interest (e.g., an enzyme having a specified enzyme activity), (ii) biomolecules (e.g., polynucleotides or enzymes having such activity (including the amino acid sequence thereof)) and (iii) produce recombinant biomolecules or bioactivities.

Suitable clones (e.g., 1-1000 or more clones) from the library are identified by the methods of the invention and sequenced using, for example, high through-put sequencing techniques. The exact method of sequencing is not a limiting factor of the invention. Any method useful in identifying the sequence of a particular cloned DNA sequence can be used. In general, sequencing is an adaptation of the natural process of DNA replication. Therefore, a template (e.g., the vector) and primer sequences are used. One general template preparation and sequencing protocol begins with automated picking of bacterial colonies, each of which contains a separate DNA clone, which will function as a template for the sequencing reaction. The selected clones are placed into media, and grown overnight. The DNA templates are then purified from the cells and suspended in water. After DNA quantification, high-throughput sequencing is performed using a sequencers, such as Applied Biosystems, Inc., Prism 377 DNA Sequencers. The resulting sequence data can then be used in additional methods, including searching a database or databases.

A number of source databases are available that contain either a nucleic acid sequence and/or a deduced amino acid sequence for use with the invention in identifying or determining the activity encoded by a particular polynucleotide sequence. All or a representative portion of the sequences (e.g., about 100 individual clones) to be tested are used to search a sequence database (e.g., GenBank, PFAM or ProDom), either simultaneously or individually. A number of different methods of performing such sequence searches are known in the art. The databases can be specific for a particular organism or a collection of organisms. For example, there are databases for the C. elegans, Arabadopsis. sp., M. genitalium, M. jannaschii, E. coli, H. influenzae, S. cerevisiae and others. The sequence data of the clone is then aligned to the sequences in the database or databases using algorithms designed to measure homology between two or more sequences.

Such sequence alignment methods include, for example, BLAST (Altschul et al., 1990), BLITZ (MPsrch) (Sturrock & Collins, 1993), and FASTA (Person & Lipman, 1988). The probe sequence (e.g., the sequence data from the clone) can be any length, and will be recognized as homologous based upon a threshold homology value. The threshold value may be predetermined, although this is not required. The threshold value can be based upon the particular polynucleotide length. To align sequences a number of different procedures can be used. Typically, Smith-Waterman or Needleman-Wunsch algorithms are used. However, as discussed faster procedures such as BLAST, FASTA, PSI-BLAST can be used.

For example, optimal alignment of sequences for aligning a comparison window may be conducted by the local homology algorithm of Smith (Smith and Waterman, Adv Appl Math, 1981; Smith and Waterman, J Teor Biol, 1981; Smith and Waterman, J Mol Biol, 1981; Smith et al, J Mol Evol, 1981), by the homology alignment algorithm of Needleman (Needleman and Wuncsch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis., or the Sequence Analysis Software Package of the Genetics Computer Group, University of Wisconsin, Madison, Wis.), or by inspection, and the best alignment (i.e., resulting in the highest percentage of homology over the comparison window) generated by the various methods is selected. The similarity of the two sequences (i.e., the probe sequence and the database sequence) can then be predicted.

Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison windo", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

One example of a useful algorithm is BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands.

The BLAST algorithm also performs a statistical analysis of the similarity between two sequences (see, e.g., Karlin & Altschul, Proc. Natl. Acad. Sci. USA 90:5873 (1993)). One measure of similarity provided by BLAST algorithm is the smallest sum probability (P(N)), which provides an indication of the probability by which a match between two nucleotide sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

Sequence homology means that two polynucleotide sequences are homologous (i.e., on a nucleotide-by-nucleotide basis) over the window of comparison. A percentage of sequence identity or homology is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence homology. This substantial homology denotes a characteristic of a polynucleotide sequence, wherein the polynucleotide comprises a sequence having at least 60 percent sequence homology, typically at least 70 percent homology, often 80 to 90 percent sequence homology, and most commonly at least 99 percent sequence homology as compared to a reference sequence of a comparison window of at least 25-50 nucleotides, wherein the percentage of sequence homology is calculated by comparing the reference sequence to the polynucleotide sequence which may include deletions or additions which total 20 percent or less of the reference sequence over the window of comparison.

Sequences having sufficient homology can be further identified by any annotations contained in the database, including, for example, species and activity information. Accordingly, in a typical environmental sample, a plurality of nucleic acid sequences will be obtained, cloned, sequenced and corresponding homologous sequences from a database identified. This information provides a profile of the polynucleotides present in the sample, including one or more features associated with the polynucleotide including the organism and activity associated with that sequence or any polypeptide encoded by that sequence based on the database information. As used herein "fingerprint" or "profile" refers to the fact that each sample will have associated with it a set of polynucleotides characteristic of the sample and the environment from which it was derived. Such a profile can include the amount and type of sequences present in the sample, as well as information regarding the potential activities encoded by the polynucleotides and the organisms from which polynucleotides were derived. This unique pattern is each sample's profile or fingerprint.

In some instances it may be desirable to express a particular cloned polynucleotide sequence once its identity or activity is determined or a suggested identity or activity is associated with the polynucleotide. In such instances the desired clone, if not already cloned into an expression vector, is ligated downstream of a regulatory control element (e.g., a promoter or enhancer) and cloned into a suitable host cell. Expression vectors are commercially available along with corresponding host cells for use in the invention.

As representative examples of expression vectors which may be used there may be mentioned viral particles, baculovirus, phage, plasmids, phagemids, cosmids, fosmids, bacterial artificial chromosomes, viral nucleic acid (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, Aspergillus, yeast, and the like). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9 (Qiagen), psiX174, pBluescript SK, pBluescript KS, pNH8A, pNH16a, pNH 18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene), pSVK3, pBPV, pMSG, pSVL (Pharmacia). However, any other plasmid or vector may be used as long as they are replicable and viable in the host.

The nucleic acid sequence in the expression vector is operatively linked to an appropriate expression control sequence(s) (promoter) to direct mRNA synthesis. Particular named bacterial promoters include lac, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors typically contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The nucleic acid sequence(s) selected, cloned and sequenced as hereinabove described can additionally be introduced into a suitable host to prepare a library, which is screened for the desired biomolecule or bioactivity. The selected nucleic acid is preferably already in a vector which includes appropriate control sequences whereby a selected nucleic acid encoding a biomolecule or bioactivity may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. The selection of an appropriate host is deemed to be within the scope of those skilled in the art from the teachings herein.

In some instances it may be desirable to perform an amplification of the nucleic acid sequence present in a sample or a particular clone that has been isolated. In this aspect, the nucleic acid sequence is amplified by PCR reaction or similar reaction known to those of skill in the art. Commercially available amplification kits are available to carry out such amplification reactions.

In addition, it is important to recognize that the alignment algorithms and searchable database can be implemented in computer hardware, software or a combination thereof. Accordingly, the isolation, processing and identification of nucleic acid or polypeptide sequences can be implemented in an automated system.

In addition to the sequence-based techniques described above, a number of traditional assay system exist for measuring an enzymatic activity using multi-well plates. For example, existing screening technology usually relies on two-dimensional well (e.g., 96-, 384- and 1536-well ) plates. The present invention also provides a capillary array-based approach of that has numerous advantages over well-based screening techniques, including the elimination of the need for fluid dispensers for dispensing fluids (e.g., reactants) into individual well reservoirs, and the reduced cost per array (e.g., glass capillaries are reusable) (see, for example, U.S. patent application Ser. No. 09/444,112, filed Nov. 22, 1999, which is incorporated herein by reference in its entirety).

Accordingly, the capillaries, capillary array and systems of the invention are particularly well suited for screening libraries for activity or biomolecules of interest including polynucleotides. The screening for activity may be effected on individual expression clones or may be initially effected on a mixture of expression clones to ascertain whether or not the mixture has one or more specified activities. If the mixture has a specified activity, then the individual clones may be re-screened for such activity or for a more specific activity after collection from the capillary array.

Chiral Selections—Aldolases

The invention provides a novel and extremely powerful selection for the discovery of new enantioselective aldolases from polypeptide or nucleic acid libraries, e.g., DNA libraries, e.g., environmental DNA or polypeptide libraries.

Aldolase Selections

Figure 9:
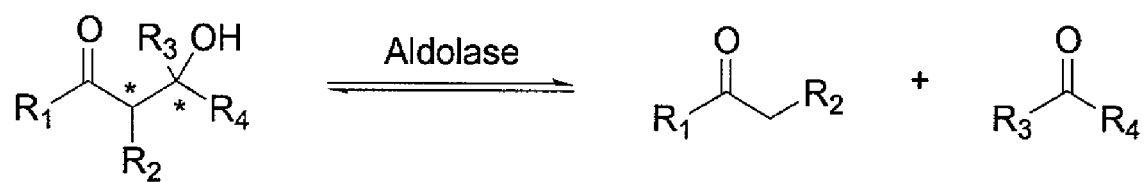
FIG. 9 illustrates a general scheme for the selection of aldolases.

Selections are the amongst most powerful methods for screening the greatest number of clones in the shortest period of time. Using the appropriate substrates and host strains, many different kinds of aldolases can be selected for by driving aldol reactions in the retro direction as shown in FIG. 9. The key components of this approach are:

General approach for the discovery of any aldolase that can give a product in the retro-aldol reaction that can be used as a selective growth source for clones containing said aldolase.

Can be a highly targeted and exquisitely specific method; utilizes the chiral desired product of the forward aldolase reaction as the selection substrate for the discovery of appropriate aldolases in reverse aldolase selection reactions.

Figure 10:
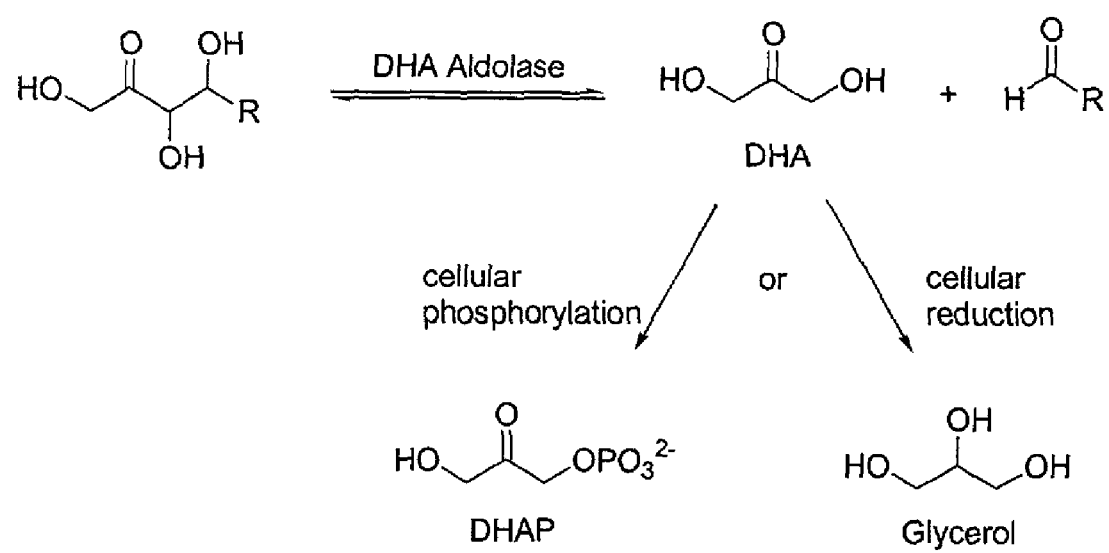
FIG. 10 illustrates a selection scheme utilizing DHA as sole carbon source, where rare DHA-dependent enzymes are selected over the ubiquitous DHAP-dependant aldolases.

An exemplary method is shown in FIG. 10, a selection scheme utilizing DHA as sole carbon source, where rare DHA-dependent enzymes are selected over the ubiquitous DHAP-dependant aldolases, which have expensive phosphorylation dependence.

Figure 11:
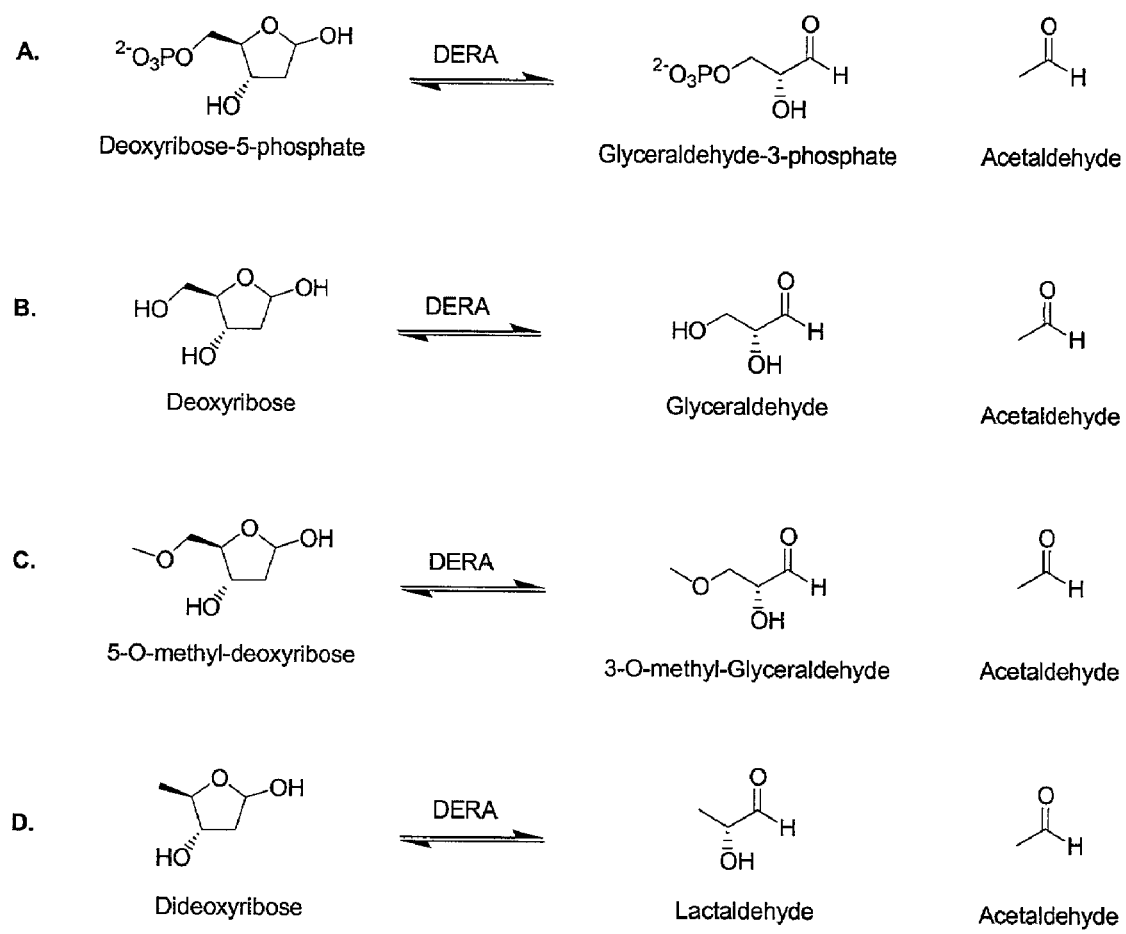
FIG. 11 illustrates exemplary methods for retro-aldol selection approaches, i.e., DERA-type aldolase selections.

Exemplary methods for retro-aldol selection approaches are illustrated in FIG. 11 (DERA-type Aldolase Selections) for the discovery of deoxyribose-5-phosphate aldolases (DERA). Several exemplary approaches are illustrated.

Figure 4:
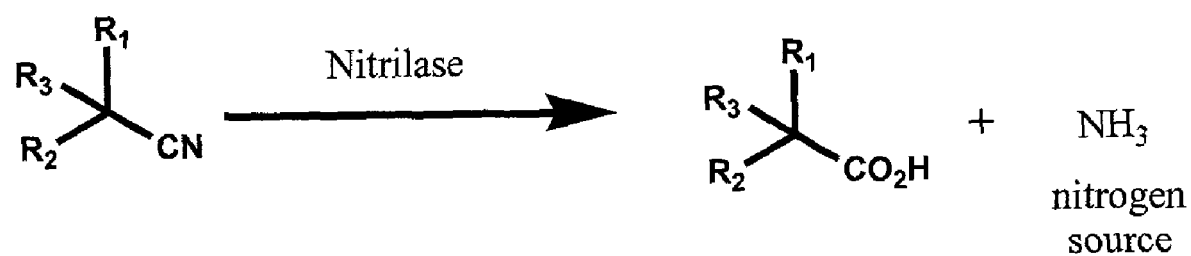
FIG. 4 is a schematic illustration of the hydrolysis of a nitrile-containing compound into the corresponding carboxylic acid and ammonia, catalyzed by a nitrilase.

In examples A to D of FIG. 11, the growth selection can be developed by running the aldolase reaction in the reverse direction, and coupling acetaldehyde production to aldehyde dehydrogenase. In A, the natural substrate, deoxyribose-5-phosphate, is used to discover new DERA enzymes. While powerful, this may result in only enzymes that require phosphorylated acceptor substrates. In many cases, it is desirable to use non-phosphorylated substrates. In FIG. 4 (B), a selection with a non-phosphorylated substrate is shown. Hits from such a discovery assay would have already been selected not to require phosphorylated substrates and thus may have a greater synthetic utility.

Both routes A and B of FIG. 11 produce acetaldehyde that can be used as a selective growth source in specific strains (see below). In addition, the co-products of the retro aldol selection reactions (glyceraldehydes-3-phosphate for A, and glyceraldehyde in B) can also be used as growth sources.

In route B of FIG. 11, there is a possibility that 2-deoxyribose can be phosphorylated in vivo in the selection host. If this occurs, then aldolases that require the phosphorylated substrate will be selected for. Routes C and D address this concern. In route C the 5' hydroxyl group is methylated and in route D, dideoxyribose is used which lacks the 5' hydroxyl group altogether. These substrates have been synthesized at Diversa. Both routes C and D still produce acetaldehyde which can be used as a sole carbon source.

Strains For Growth on Ethanol and Acetaldehyde

Figure 12:
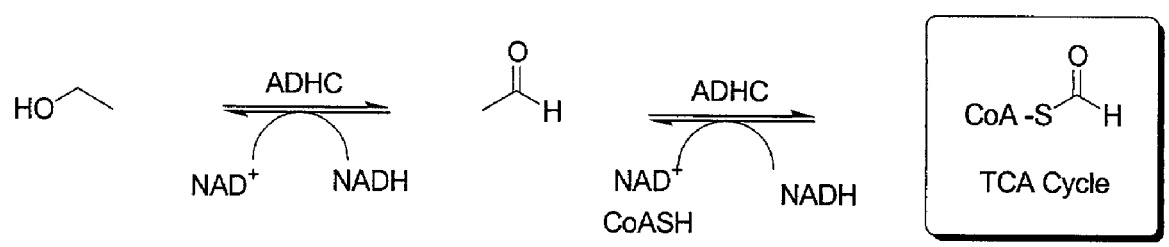
FIG. 12 illustrates the metabolism of ethanol and acetaldehyde by selection strains.

Growth on ethanol or acetaldehyde is a crucial element of many selection schemes including those for the DERA selections. In random mutagenesis studies, Clark and co-workers have found that mutants constitutively expressing alcohol dehydrogenase (ADH) were able to grow on ethanol as a sole C-source. In a two-step transformation, ADH converts ethanol to acetaldehyde and then to acetyl-CoA, which serves as a carbon source, entering into the citric acid cycle (TCA cycle); see FIG. 12 (illustrating the metabolism of ethanol and acetaldehyde by selection strains). In wild-type *E. coli*, ADH functions in the reverse direction recycling reduced NAD under anaerobic conditions. A single amino acid mutation in the wild-type ADH has been shown to be responsible for aerobic activity and a mutation in the promoter confers constitutive expression (see, e.g., J. Bacteriol. 1980 141, 177-183; b. J. Bacteriol. 1980 144, 179-184).

Strain Development

The invention uses *E. coli* strains capable of growing on ethanol as a sole C-source. Two approaches have been implemented, one utilizing a chromosomally expressed alcohol dehydrogenase (ADH) and the other utilizing a plasmid-borne ADH. These strains have been engineered to be compatible with any library for use in selections.

Figure 13:
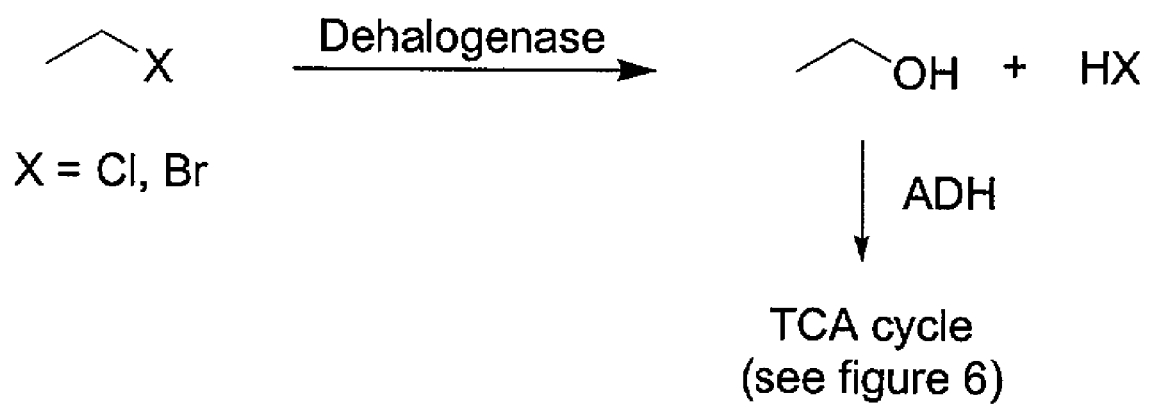
FIG. 13 illustrates an exemplary selection strategy for novel dehalogenases.

Strains that grow on ethanol under aerobic conditions can be used. In addition, we have found that acetaldehyde serves as a sole C-source for growth. Thus, any enzymatic reaction generating either ethanol or acetaldehyde can be selected for using these strains. Application of these strains to aldolase discovery has already been discussed, above. Another useful example is for the discovery of hydrolytic haloalkane dehalogenases as shown in FIG. 13 (illustrating a selection strategy for novel dehalogenases).

Enantioselective Screening of Epoxide Hydrolases via Selections

Selection assays, in which only the clones containing activities of interest grow, are very powerful for new enzyme discovery because they offer exceptionally high throughput. This approach is especially powerful when applied to environmental DNA libraries. The invention provides an approach to discover and evolve epoxide hydrolases using a novel selection strategy. The approach relies on utilizing epoxide substrates that can be converted by epoxide hydrolases to diols that can be utilized by host bacteria as a carbon source. When environmental library cells are grown in minimal media supplemented with this epoxide as the sole carbon source, only those clones harboring active epoxide hydrolases will be able to produce the corresponding diol and to utilize it as a carbon source for growth and proliferation. Over time, these clones will dominate the microbial population, and thus can be readily isolated. If the selected diols are chiral and enantiomerically pure, this selection method may be used for screening epoxide hydrolases with preference toward one enantiomeric form over the other, thus resulting the discovery of epoxide hydrolases with high enantioselectivity.

Figure 14:
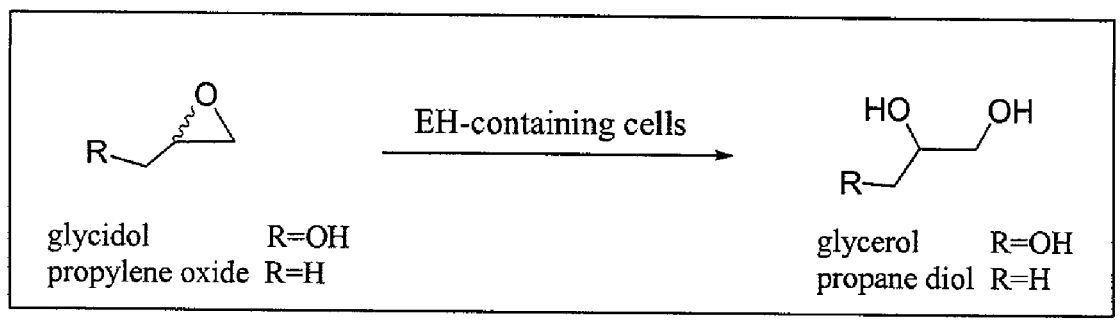
FIG. 14 illustrates an exemplary selection strategy using two chiral epoxides, glycidol and propylene oxide, used as selection substrates.

For example, two chiral epoxides, glycidol and propylene oxide, can be used as selection substrates for the above described purpose, see FIG. 14. The corresponding vicinal diols, glycerol, propane diol, are known to support the growth of *E. coli* or its mutants as sole carbon sources. When pure enantiomers of glycidol or propylene oxide are used for selections, epoxide hydrolases with selectivity for these enantiomers may be discovered.

Figure 15:
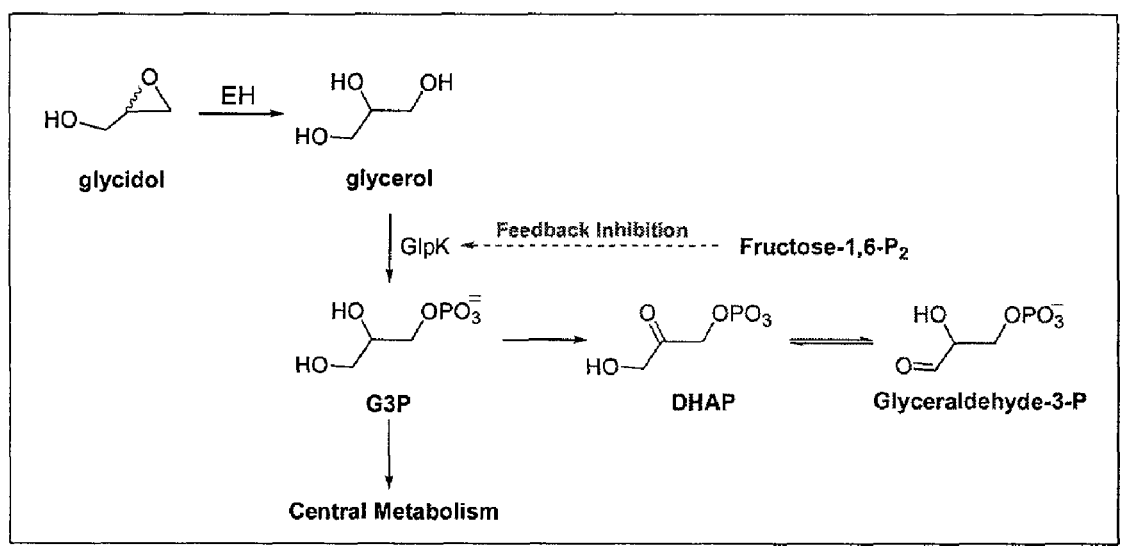
FIG. 15 illustrates the glycerol metabolic pathway.

Appropriate hosts need to be developed for the selection experiments. For example, an *E. coli* mutant with mutations in the glycerol metabolic pathway genes glpK and glpR may be required to facilitate glycerol utilization (see, e.g., Maloy, S. R.; Nunn, W. D. J. Bacteriol. 1982, 149, 173-180). See FIG. 15, illustrating the glycerol metabolic pathway.

Figure 16:
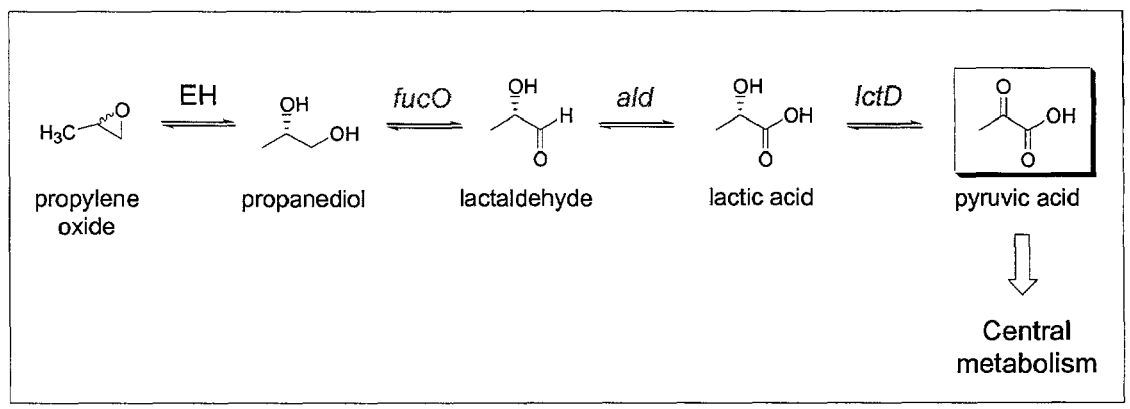
FIG. 16 illustrates an exemplary propylene oxide conversion process to pyruvic acid.

Also, an *E. coli* mutant with a constitutively expressed oxidoreductase (fucO) that can convert propane diol to lactaldehyde is required for propylene oxide to be used as carbon source for selection (see, e.g., Hacking, A. J.; Lin, E. C. C. J. Bacteriol. 1976, 126, 1166-1172). See FIG. 16 illustrating a propylene oxide conversion process to pyruvic acid. Additional epoxide substrates for selection may also be identified if *E. coli* mutants capable of growing on their corresponding vicinal diols.

Results. Epoxides are known to be toxic to microbes due to alkylation of proteins and nucleic acids. The tolerance of *E. coli* cells to epoxide compounds have been evaluated. In our preliminary experiments, we evaluated the effect of different concentrations of glycidol and propylene oxide on the growth of an *E. coli* host. The results showed that *E. coli* can tolerate up to 10 mM of glycidol and propylene oxide. This concentration may be high enough for selections as it was found that the cells were able to grow with 5 mM glycerol provided extracellularly in the media as the sole carbon source.

In addition, a propane diol-utilizing *E. coli* mutant and an *E. coli* mutant that can utilize glycerol more efficiently than the wild-type have been obtained from the *E. coli* Genetic Stock Center (CGSC) at Yale University. These hosts have been further engineered to be ready for use in selections.

Capillary Array Systems

The invention provides systems and methods for selecting a nucleic acid encoding an enantioselective enzyme and selecting enantioselective enzymes using capillary arrays, such as GIGAMATRIX™, Diversa Corporation, San Diego, Calif. The capillary arrays of the invention provide a system and method for "retaining" or "holding" nucleic acid and polypeptide samples to be analyzed. The nucleic acid and polypeptide samples (including reagents, substrates, etc.) can be directly or indirectly "held" onto a capillary wall. The cells in the cell-based methods can be directly or indirectly "held" within a capillary lumen. In one aspect, the capillary array apparatus includes a plurality of capillaries formed into an array of adjacent capillaries, wherein each capillary comprises at least one wall defining a lumen for "retaining" a sample. The apparatus can further include interstitial material disposed between adjacent capillaries in the array, and one or more reference indicia formed within of the interstitial material. The capillary can be adapted for being bound in an array of capillaries; e.g., it can include a first wall defining a lumen for retaining the sample and a second wall formed of a filtering material. The filtering material can, e.g., filter excitation energy provided to the lumen to excite the sample.

In one aspect, the capillary array includes a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a microtiter plate having about 100,000 or more individual capillaries bound together.

The capillaries can be formed with an aspect ratio of 50:1. In one aspect, each capillary has a length of approximately 10 mm, and an internal diameter of the lumen of approximately 200 µm. However, other aspect ratios are possible, and range from 10:1 to well over 1000:1. Accordingly, individual capillaries have an inner diameter that ranges from 10-500 µm. A capillary having an internal diameter of 200 µm and a length of 1 cm has a volume of about 0.3 µl. The length and width of each capillary can be based on a desired volume and other characteristics, such as evaporation rate, etc. The capillary array can have a density of 500 to more than 1,000 capillaries per $cm^2$, or about 5 capillaries per $mm^2$. The capillary array can be formed to a width or diameter of about 0.5-20 mm and a height or thickness of 0.05 to about 10 cm. The capillary array can have a thickness of about 0.1 to about 5 cm.

The capillaries can be made according to various manufacturing techniques. In one aspect, the capillaries are manufactured using a hollow-drawn technique. A cylindrical, or other hollow shape, portion of glass is drawn out to continually longer lengths according to known techniques. The glass is drawn to a desired diameter and then cut into portions of a specific length to form a capillary according to the invention. Then, a number of individual capillaries are bound together in an array. In an alternative aspect, a glass etching process is used. A solid tube of glass can be drawn out to a particular width, and cut into portions of a specific length. Then, each solid tube portion is center-etched with acid to form a capillary. The tubes can be bound before or after the etch process.

A large number of materials can be suitably used to form a capillary array according to the invention and depending on the manufacturing technique used, including without limitation, glass, metal, semiconductors such as silicon, quartz, ceramics, or various polymers and plastics including, among others, polyethylene, polystyrene, and polypropylene. The internal walls of the capillary array, or portions thereof, may be coated or silanized to modify their surface properties (e.g., to immobilize nucleic acid to be sequenced). For example, the hydrophilicity or hydrophobicity may be altered to promote or reduce wicking or capillary action, respectively. The coating material includes, for example, ligands such as avidin, streptavidin, antibodies, antigens, and other molecules having, e.g., specific binding affinity or that can withstand thermal or chemical sterilization.

A capillary array may optionally include reference indicia for providing a positional or alignment reference. The reference indicia may be formed of a pad of glass extending from the surface of the capillary array, or embedded in the interstitial material. In one aspect, the reference indicia are provided at one or more corners of a microtiter plate formed by the capillary array. A corner of the plate or set of capillaries may be removed, and replaced with the reference indicia. The reference indicia may also be formed at spaced intervals along a capillary array, to provide an indication of a subset of capillaries.

The capillary can include a first wall defining a lumen and a second wall surrounding the first wall. In one aspect, the second wall has a lower index of refraction than the first wall. In one aspect, the first wall is a sleeve glass having a high index of refraction, forming a waveguide in which light from excited fluorophores travels. The second wall can be black EMA glass, having a low index of refraction, forming a cladding around the first wall against which light is refracted and directed along the first wall for total internal reflection within the capillary. The second wall can thus be made with any material that reduces the "cross-talk" or diffusion of light between adjacent capillaries. Alternatively, the inside surface of the first wall can be coated with a reflective substance to form a mirror, or mirror-like structure, for specular reflection within the lumen. Many different materials can be used in forming the first and second walls, creating different indices of refraction for desired purposes. A filtering material can be formed around the lumen to filter energy to and from the lumen. In one aspect, the inner wall of the first wall of each capillary of the array, or portion of the array, is coated with the filtering material. In another aspect, the second wall includes the filtering material. For instance, the second wall can be formed of the filtering material, such as filter glass for example, or in one aspect, the second wall is EMA glass that is doped with an appropriate amount of filtering material. The filtering material can be formed of a color other than black and tuned for a desired excitation/emission filtering characteristic. The filtering material can allow transmission of excitation energy into the lumen, and blocks emission energy from the lumen except through one or more openings at either end of the capillary. When the second wall is formed with a filtering material, certain wavelengths of light representing excitation energy are allowed through to the lumen, and other wavelengths of light representing emission energy are blocked from exiting, except as directed within and along the first wall. The entire capillary array, or a portion thereof, can be tuned to a specific individual wavelength or group of wavelengths, for filtering different bands of light in an excitation and detection process (e.g., to determine an enzyme reaction product).

Expression Vectors and Cassettes

The nucleic acids and libraries, e.g., environmental libraries, used in the methods of the invention can be inserted and expressed in any expression system, e.g., simple promoters, plasmids, vectors, recombinant viruses, mammalian and human artificial chromosomes, satellite artificial chromosomes, yeast artificial chromosomes, bacterial artificial chromosomes, P1 artificial chromosomes, recombinant vectors, and the like.

Mammalian artificial chromosomes (MACs) and human artificial chromosomes (HAC) are, e.g., described in Ascenzioni (1997) Cancer Lett. 118:135-142; Kuroiwa (2000) Nat. Biotechnol. 18:1086-1090; U.S. Pat. Nos. 5,288,625; 5,721,118; 6,025,155; 6,077,697). MACs can contain inserts larger than 400 kilobase (Kb), see, e.g., Mejia (2001) Am. J. Hum. Genet. 69:315-326. Auriche (2001) EMBO Rep. 2:102-107, has built a human minichromosomes having a size of 5.5 kilobase. Satellite artificial chromosomes, or, satellite DNA-based artificial chromosomes (SATACs), are, e.g., described in Warburton (1997) Nature 386:553-555; Roush (1997) Science 276:38-39; Rosenfeld (1997) Nat. Genet. 15:333-335). SATACs can be made by induced de novo chromosome formation in cells of different mammalian species; see, e.g., Hadlaczky (2001) Curr. Opin. Mol. Ther. 3:125-132; Csonka (2000) J. Cell Sci. 113 ( Pt 18):3207-3216. Yeast artificial chromosomes (YACs) can also be used and typically contain inserts ranging in size from 80 to 700 kb. YACs have been used for many years for the stable propagation of genomic fragments of up to one million base pairs in size; see, e.g., U.S. Pat. Nos. 5,776,745; 5,981,175; Feingold (1990) Proc. Natl. Acad. Sci. USA 87:8637-8641; Tucker (1997) Gene 199:25-30; Adam (1997) Plant J.11:1349-1358; Zeschnigk (1999) Nucleic Acids Res. 27:21. Bacterial artificial chromosomes (BACs) are vectors that can contain 120 Kb or greater inserts, see, e.g., U.S. Pat. Nos. 5,874,259; 6,277,621; 6,183,957. BACs are based on the *E. coli* F factor plasmid system and simple to manipulate and purify in microgram quantities. Because BAC plasmids are kept at one to two copies per cell, the problems of rearrangement observed with YACs, which can also be employed in the present methods, are eliminated; see, e.g., Asakawa (1997) Gene 69-79; Cao (1999) Genome Res. 9:763-774. P1 artificial chromosomes (PACs), bacteriophage P1-derived vectors are, e.g., described in Woon (1998) Genomics 50:306-316; Boren (1996) Genome Res. 6:1123-1130; Ioannou (1994) Nature Genet. 6:84-89; Reid (1997) Genomics 43:366-375; Nothwang (1997) Genomics 41:370-378; Kern (1997) Biotechniques 23:120-124). P1 is a bacteriophage that infects *E. coli* that can contain 75 to 100 Kb DNA inserts (see, e.g., Mejia (1997) Genome Res 7:179-186; Ioannou (1994) Nat Genet 6:84-89). PACs are screened in much the same way as lambda libraries. See also Ashworth (1995) Analytical Biochem. 224:564-571; Gingrich (1996) Genomics 32:65-74. Other cloning vehicles can also be used, for example, recombinant viruses; cosmids, plasmids or cDNAs; see, e.g., U.S. Pat. Nos. 5,501,979; 5,288,641; 5,266,489. These vectors can include marker genes, such as, e.g., luciferase and green fluorescent protein genes (see, e.g., Baker (1997) Nucleic Acids Res 25:1950-1956). Sequences, inserts, clones, vectors and the like can be isolated from any natural sources, obtained from such sources as ATCC or GenBank libraries or commercial sources, or prepared by synthetic or recombinant methods. The nucleic acids and libraries of the invention can also be inserted and expressed in "expression cassettes," which comprise sequences capable of affecting expression of a structural gene (i.e., a protein coding sequence, such as an enzyme to be selected) in a host compatible with such sequences. Expression cassettes can include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like. A "vector" comprises a nucleic acid that can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The phrases "nucleic acid" or "nucleic acid sequence" as used herein refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin.

All headings and subheading used herein are provided for the convenience of the reader and should not be construed to limit the invention.

As used herein and in the appended claims, the singular forms "a," "and," and "the" include plural referents unless the context clearly dictates otherwise. Thus, for example, reference to "a clone" includes a plurality of clones and reference to "the nucleic acid sequence" generally includes reference to one or more nucleic acid sequences and equivalents thereof known to those skilled in the art, and so forth.

Unless defined otherwise, all technical and scientific terms used herein have the same meaning as commonly understood to one of ordinary skill in the art to which the invention belongs. Although any methods, devices and materials similar or equivalent to those described herein can be used in the practice or testing of the invention, the preferred methods, devices and materials described.

All publications mentioned herein are incorporated herein by reference in full for the purpose of describing and disclosing the databases, proteins, and methodologies, which are described in the publications, which might be used in connection with the described invention. The publications discussed above and throughout the text are provided solely for their disclosure prior to the filing date of the present application. Nothing herein is to be construed as an admission that the inventors are not entitled to antedate such disclosure by virtue of prior invention.

The invention will be further described with reference to the following examples; however, it is to be understood that the invention is not limited to such examples.

EXAMPLES

Example 1

Figure 6:
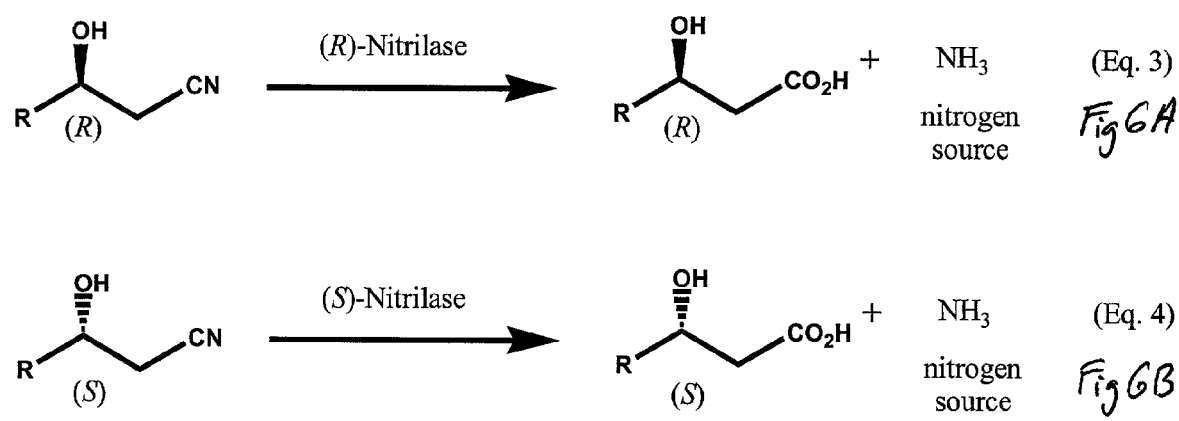
FIGS. 6A and 6B are illustrations of exemplary methods of the invention, wherein only a) cells that can effectively hydrolyze the R form of a β-hyroxynitrile will survive (Eq. 3); and, b) only cells that can effectively hydrolyze the S form of a β-hyroxynitrile will survive (Eq. 4).
Figure 7:
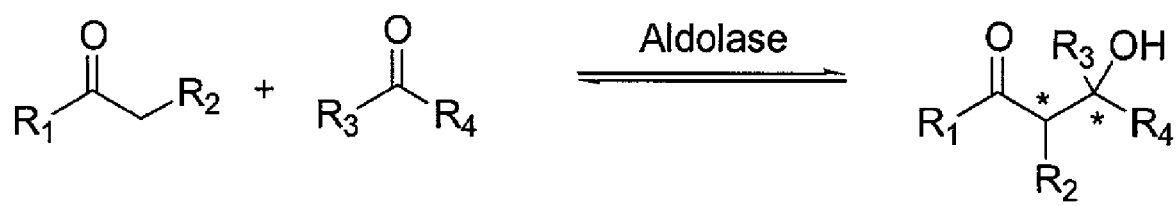
FIG. 7 illustrates an aldolase reaction catalyzing the formation of carbon-carbon bonds through the aldol reaction.
Figure 8:
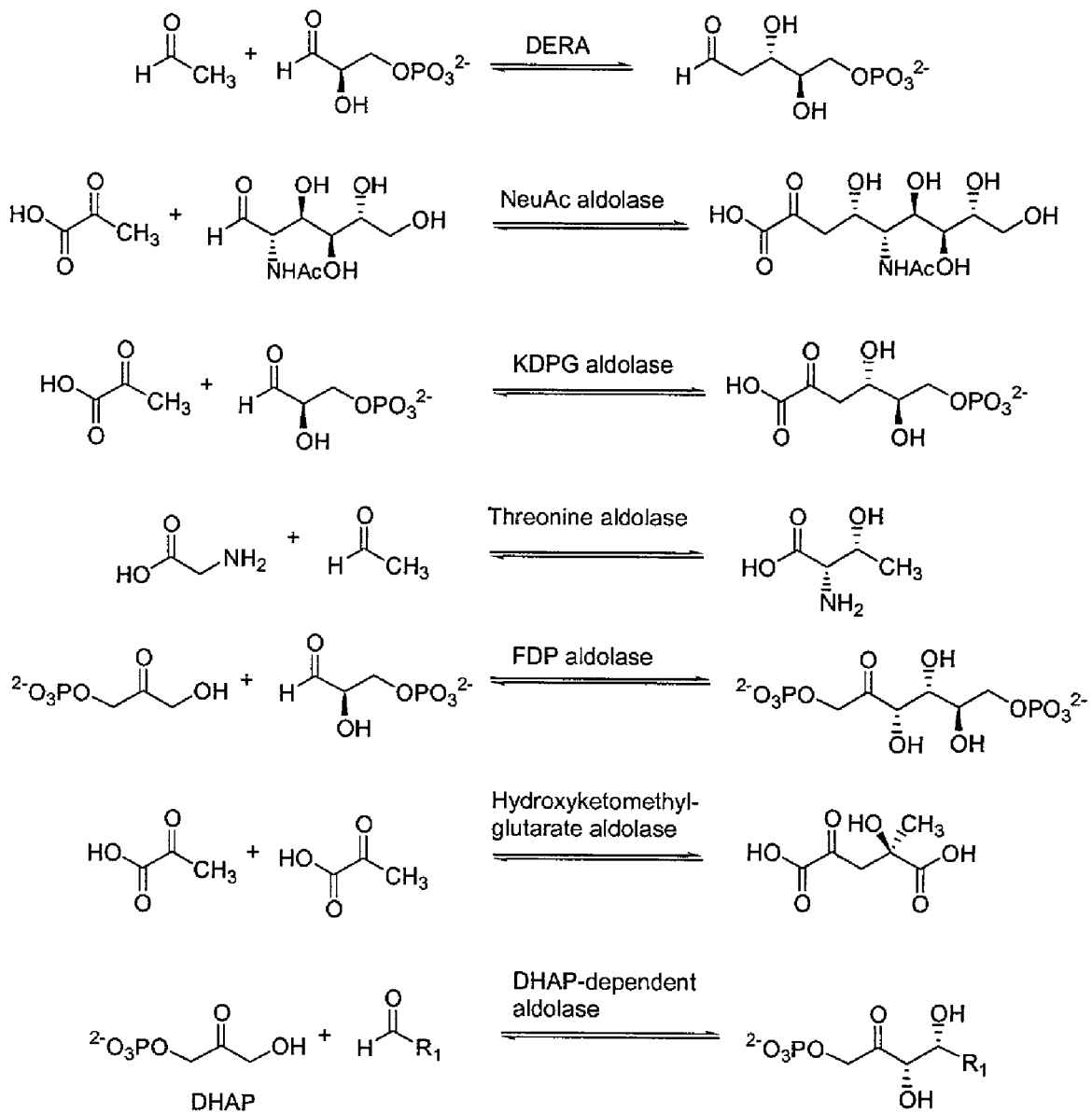
FIG. 8 illustrates a few well-characterized examples of reactions catalyzed by aldolases.

Selection of Enzymes which can Hydrolyze Individual Enantiomers of a β-hydroxynitrile In the present example, the individual enantiomers of a β-hydroxynitrile are used as substrates for selection of nitrilase enzymes that offer opposite stereoselectivity in the hydrolysis of the substrate. This example is illustrated in FIG. 6.

Here, only cells that can hydrolyze the (R)-hydroxynitrile will survive in FIG. 6A (Eq. 3), while selection for cells that can effectively hydrolyze the (S)-hydroxynitrile is shown in FIG. 6B (Eq. 4). Only a) cells that can effectively hydrolyze the R form of a β-hyroxynitrile will survive (Eq. 3); and, b) only cells that can effectively hydrolyze the S form of a β-hyroxynitrile will survive (Eq. 4).

Example 2

DNA Isolation

DNA is isolated using the IsoQuick Procedure as per manufacture's instructions (Orca Research Inc., Bothell, Wash.). The isolated DNA can optionally be normalized according to Example 2 (below). Upon isolation, the DNA is sheared by pushing and pulling the DNA through a 25-gauge double-hub needle and a 1-cc syringe about 500 times. A small amount is run on a 0.8% agarose gel to make sure the majority of the DNA is in the desired size range (about 3-6kb).

Blunt-ending DNA. The DNA is blunt-ended by mixing 45 µl of 10×Mung Bean Buffer, 2.0 µl Mung Bean Nuclease (1050 u/µl) and water to a final volume of 405 µl. The mixture is incubated at 37° C. for 15 minutes. The mixture is phenol; chloroform extracted, followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol and repelleted in the microcentrifuge. Following centrifugation, the DNA is dried and gently resuspended in 26 µl of TE buffer.

Methylation of DNA. The DNA is methylated by mixing 4 µl of 10×EcoRI Methylase Buffer, 0.5 µl SAM (32 mM), 5.0 µl EcoRI Methylase (40 u/µl) and incubating at 37° C. for 1 hour. In order to insure blunt ends, the following can be added to the methylation reaction: 5.0 µl of 100 mM $MgCl_2$, 8.0 µl of dNTP mix (2.5 mM of each dGTP, dATP, dTTP, dCTP), 4.0 µl of Klenow (5 u/µl). The mixture is then incubated at 12° C. for 30 minutes.

After incubating for 30 minutes 450 µl 1×STE is added. The mixture is phenol/chloroform extracted once followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol, repelleted in the microcentrifuge and allowed to dry for 10 minutes.

Ligation. The DNA is ligated by gently resuspending the DNA in 8 µlEcoRI adapters (from Stratagene's cDNA Synthesis Kit), 1.0 µl of 10×ligation buffer, 1.0 µl of 10 mM rATP, 1.0 µl of T4 DNA Ligase (4u/µl) and incubating at 4° C. for 2 days. The ligation reaction is terminated by heating for 30 minutes at 70° C.

Phosphorylation of adapters. The adapter ends are phosphorylated by mixing the ligation reaction with 1.0 µl of 10× Ligation Buffer, 2.0 µl of 10 mM rATP, 6.0 µl of $H_2O$, 1.0 µl of polynucleotide kinase (PNK), and incubating at 37° C. for 30 minutes. After incubating for 30 minutes, 31 µl of $H_2O$ and 5 ml of 10× STE are added to the reaction and the sample is size fractionated on a Sephacryl S-500 spin column. The pooled fractions (1-3) are phenol/chloroform extracted once, followed by an additional chloroform extraction. The DNA is precipitated by the addition of ice cold ethanol on ice for 10 minutes. The precipitate is pelleted by centrifugation in a microcentrifuge at high speed for 30 minutes. The resulting pellet is washed with 1 ml 70% ethanol, repelleted by centrifugation and allowed to dry for 10 minutes. The sample is resuspended in 10.5 µl TE buffer. The sample is not plated, but is ligated directly to lambda arms as described above, except 2.5 µl of DNA and no water is used.

Sucrose Gradient (2.2 ml) Size Fractionation. Ligation is stopped by heating the sample to 65° C. for 10 minutes. The sample is gently loaded on a 2.2 ml sucrose gradient and centrifuged in a mini-ultracentrifuged 45k rpm at 20° C. for 4 hours (no brake). Fractions are collected by puncturing the bottom of the gradient tube with a 20-gauge needle and allowing the sucrose to flow through the needle. The first 20 drops are collected in a Falcon 2059 tube, and then ten 1-drop fractions (labeled 1-10) are collected. Each drop is about 60 µl in volume. Five µl of each fraction are run on a 0.8% agarose gel to check the size. Fractions 1-4 (about 10-1.5 kb) are pooled and, in a separate tube, fractions 5-7 (about 5-0.5 kb) are pooled. One ml of ice cold ethanol is added to precipitate the DNA and then placed on ice for 10 minutes. The precipitate is pelleted by centrifugation in a microcentrifuge at high speed for 30 minutes. The pellets are washed by resuspending them in 1 ml of 70% ethanol and repelleting them by centrifugation in a microcentrifuge at high speed for 10 minutes, and then dried. Each pellet is then resuspended in 10 µl of TE buffer.

Test Ligation to Lambda Arms. The assay is plated by spotting 0.5 µl of the sample on agarose containing ethidium bromide along with standards (DNA sample of known concentration) to get an approximate concentration. The samples are then viewed using UV light and the estimated concentration is compared to the standards.

The following ligation reaction (5 µl reactions) are prepared and incubated at 4° C. overnight, as shown in Table 1 below:

TABLE 1

| Sample | H₂O | 10X Ligase | 10 mM rATP | Lambda arms (ZAP) | Insert DNA | T4 DNA Ligase |
|---|---|---|---|---|---|---|
| Fraction 1-4 | 0.5 µl | 0.5 µl | 0.5 µl | 1.0 µl | 2.0 µl | 0.5 µl |
| Fraction 5-7 | 0.5 µl | 0.5 µl | 0.5 µl | 1.0 µl | 2.0 µl | 0.5 µl |

Test Package and Plate. The ligation reactions are packaged following manufacturer's protocol. Packaging reactions are stopped with 500 µl SM buffer and pooled with packaging that came from the same ligation. One 4 µl of each pooled reaction is titered on an appropriate host ($OD_{600}$=1.0) (XL1-Blue MRF). 200 µl host (in $MgSO_4$) are added to Falcon 2059 tubes, inoculated with 1 µl packaged phage and incubated at 37° C. for 15 minutes. About 3 ml of 48° C. top agar (50 ml stock containing 150 µl IPTG (0.5 M) and 300 µl X-GAL (350 mg/ml)) are added and plated on 100 mm plates. The plates are incubated overnight at 37° C.

Amplification of Libraries ($5.0 \times 10^5$ recombinants from each library). About 3.0 ml host cells ($OD_{600}$=1.0) are added to two 50 ml conical tubes, inoculated with $2.5 \times 10^5$ pfu of phage per conical tube, and then incubated at 37°C. for 20 minutes. Top agar is added to each tube to a final volume of 45 ml. Each tube is plated across five 150 mm plates. The plates are incubated at 37° C. for 6-8 hours or until plaques are about pin-head in size. The plates are overlaid with 8-10 ml SM Buffer and placed at 4° C. overnight (with gentle rocking if possible).

Harvest Phage. The phage suspension is recovered by pouring the SM buffer off each plate into a 50 ml conical tube. About 3 ml of chloroform are added, shaken vigorously and incubated at room temperature for 15 minutes. The tubes are centrifuged at 2K rpm for 10 minutes to remove cell debris. The supernatant is poured into a sterile flask, 500 µl chloroform are added and stored at 4° C.

Titer Amplified Library. Serial dilutions of the harvested phage are made (for example, $10^{-5}$=1 µl amplified phage in 1 ml SM Buffer; $10^{-6}$=1 µl of the $10^{-3}$ dilution in 1 ml SM Buffer and the like), and 200 µl host (in 10 mM $MgSO_4$) are added to two tubes. One tube is inoculated with 10 µl of $10^{-6}$ dilution ($10^{-5}$). The other tube is inoculated with 1 µl of $10^{-6}$ dilution ($10^{-6}$), and incubated at 37° C. for 15 minutes.

About 3 ml of 48° C. top agar (50 ml stock containing 150 µl IPTG (0.5 M) and 37 µl X-GAL (350 mg/ml)) are added to each tube and plated on 100 mm plates. The plates are incubated overnight at 37° C.

The ZAP II library is excised to create the pBLUESCRIPT library according to manufacturer's protocols (Stratagene).

The DNA library can be transformed into host cells (e.g., *E. coli*) to generate an expression library of clones.

Example 3

Normalization

Prior to library generation, purified DNA can be normalized. DNA is first fractionated according to the following protocol A sample composed of genomic DNA is purified on a cesium-chloride gradient. The cesium chloride (Rf=1.3980) solution is filtered through a 0.2 µm filter and 15 ml is loaded into a 35 ml OptiSeal tube (Beckman) The DNA is added and thoroughly mixed. Ten micrograms of bis-benzimide (Sigma; Hoechst 33258) is added and mixed thoroughly. The tube is then filled with the filtered cesium chloride solution and spun in a Bti50 rotor in a Beckman L8-70 Ultracentrifuge at 33 k rpm for 72 hours. Following centrifugation, a syringe pump and fractionator (Brandel Model 186) are used to drive the gradient through an ISCO UA-5UV absorbance detector set to 280 nm. Peaks representing the DNA from the organisms present in an environmental sample are obtained. Eubacterial sequences can be detected by PCR amplification of DNA encoding rRNA from a 10 fold dilution of the *E. coli* peak using the following primers to amplify:

```
Forward primer:
5'-AGAGTTTGATCCTGGCTCAG-3'      (SEQ ID NO: 4)

Reverse primer:
5'-GGTTACCTTGTTACGACTT-3'       (SEQ ID NO: 5)
```

Recovered DNA is sheared or enzymatically digested to 3-6 kb fragments. Lone-linker primers are ligated and the DNA is size-selected. Size-selected DNA is amplified by PCR, if necessary.

Normalization is then accomplished by resuspending the double-stranded DNA sample in hybridization buffer (0.12 M $NaH_2PO_4$, pH 6.8/0.82 M NaCl/1 mM EDTA/0.1% SDS). The sample is overlaid with mineral oil and denatured by boiling for 10 minutes. The sample is incubated at 68° C. for 12-36 hours. Double-stranded DNA is separated from single-stranded DNA according to standard protocols (Sambrook, 1989) on hydroxylapatite at 60° C. The single-stranded DNA fraction is desalted and amplified by PCR. The process is repeated for several more rounds (up to 5 or more).

Example 4

Construction of a Stable, Large Insert DNA Library of Picoplankton Genomic DNA

Cell collection and preparation of DNA. Agarose plugs containing concentrated picoplankton cells were prepared from samples collected on an oceanographic cruise from Newport, Oregon to Honolulu, Hi. Seawater (30 liters) was collected in Niskin bottles, screened through 10 µm Nitex, and concentrated by hollow fiber filtration (Amicon DC10) through 30,000 MW cutoff polyfulfone filters. The concentrated bacterioplankton cells were collected on a 0.22 µm, 47 mm Durapore filter, and resuspended in 1 ml of 2×STE buffer (1 M NaCl, 0.1M EDTA, 10 mM Tris, pH 8.0) to a final density of approximately $1 \times 10^{10}$ cells per ml. The cell suspension was mixed with one volume of 1% molten Seaplaque LMP agarose (FMC) cooled to 40° C., and then immediately drawn into a 1 ml syringe. The syringe was sealed with parafilm and placed on ice for 10 min. The cell-containing agarose plug was extruded into 10 ml of Lysis Buffer (10 mM Tris pH 8.0, 50 mM NaCl, 0.1M EDTA, 1% Sarkosyl, 0.2% sodium deoxycholate, 1 mg/ml lysozyme) and incubated at 37° C. for one hour. The agarose plug was then transferred to 40 mls of ESP Buffer (1% Sarkosyl, 1 mg/ml proteinase K, in 0.5M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug (72 µl) prepared from a sample collected off the Oregon coast was dialyzed overnight at 4° C. against 1 mL of buffer A (100 mM NaCl, 10 mM Bis Tris Propane-HCl, 100 µg/ml acetylated BSA: pH 7.0 at 25° C.) in a 2 mL microcentrifuge tube. The solution was replaced with 250 μl of fresh buffer A containing 10 mM $MgCl_2$ and 1 mM DTT and incubated on a rocking platform for 1 hr at room temperature. The solution was then changed to 250 μl of the same buffer containing 4U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 min to inactivate the enzyme and to melt the agarose. The agarose was digested and the DNA dephosphorylased using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile $H_2O$ to a concentration of 2.5 ng/μl for ligation to the pFOS1 vector.

PCR amplification results from several of the agarose plugs indicated the presence of significant amounts of archaeal DNA. Quantitative hybridization experiments using rRNA extracted from one sample, collected at 200 m of depth off the Oregon Coast, indicated that planktonic archaea in (this assemblage comprised approximately 4.7% of the total picoplankton biomass (this sample corresponds to "PACI"-200 m in Table 1 of DeLong et al., Nature, 371:695-698, 1994). Results from archaeal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately $7.5 \times 10^5$ cells, therefore approximately $5.4 \times 10^5$ cells were present in the 72 μl slice used in the preparation of the partially digested DNA.

Vector arms were prepared from pFOS1 as described (Kim et al., Stable propagation of cosmid sized human DNA inserts in an F factor based vector, Nucl. Acids Res., 20:10832-10835, 1992). Briefly, the plasmid was completely digested with AstII, dephosphorylated with HK phosphatase, and then digested with BamHI to generate two arms, each of which contained a cos site in the proper orientation for cloning and packaging ligated DNA between 35-45 kbp. The partially digested picoplankton DNA was ligated overnight to the PFOS1 arms in a 15 μl ligation reaction containing 25 ng each of vector and insert and 1U of T4 DNA ligase (Boehringer-Mannheim). The ligated DNA in four microliters of this reaction was in vitro packaged using the Gigapack XL packaging system (Stratagene), the fosmid particles transfected to $E.\ coli$ strain DH10B (BRL), and the cells spread onto $LB_{cm\ 15}$ plates. The resultant fosmid clones were picked into 96-well microliter dishes containing $LB_{cm\ 15}$ml supplemented with 7% glycerol. Recombinant fosmids, each containing ca. 40 kb of picoplankton DNA insert, yielded a library of 3.552 fosmid clones, containing approximately $1.4 \times 10^8$ base pairs of cloned DNA. All of the clones examined contained inserts ranging from 38 to 42 kbp. This library was stored frozen at −80° C. for later analysis.

A number of aspects of the invention have been described. Nevertheless, it will be understood that various modifications may be made without departing from the spirit and scope of the invention. Accordingly, other aspects are within the scope of the following claims.

---

What is claimed is:

1. A method for screening an environmental nucleic acid library comprising uncharacterized nucleic acids for the presence of a nucleic acid encoding an enantioselective enzyme that can catalyze a reaction on a chiral substrate molecule to yield a factor essential for growth of a cell, wherein the factor essential for growth of the cell must be of a specific chirality to induce growth of the cell and the enantioselective enzyme can catalyze the reaction in both the forward and reverse directions,
comprising:
(a) providing an environmental nucleic acid library comprising a plurality of uncharacterized polypeptide-encoding nucleic acids;
(b) providing a plurality of cells, wherein the cells lack an active form of the enantioselective enzyme and lack the factor essential for growth of the cells, wherein the factor must be of a specific chirality to induce growth of the cells;
(c) inserting the nucleic acid library of step (a) into the cells of step (b) and incubating the cells under conditions wherein polypeptides encoded by the uncharacterized polypeptide-encoding nucleic acids of step (a) are expressed;
(d) incubating the cells in a growth medium lacking the factor essential for cell growth, and providing the chiral substrate, wherein step (c) and step (d) are not carried out in any particular order or are done together; and
(e) screening the cells for growth, wherein growth of the cells identifies the nucleic acid library as comprising a nucleic acid that encodes the enantioselective enzyme.

2. The method of claim 1, wherein the environmental nucleic acid library comprises a mixed population of organisms.

3. The method of claim 2, wherein the mixed population of organisms is derived from a soil sample, a water sample or an air sample.

4. The method of claim 1, wherein the enantioselective enzyme encoded by a nucleic acid as provided in step (a) is selected from the group consisting of a transaminase, a nitrilase, an aldolase and an epoxide hydrolase.

5. The method of claim 1, wherein the equilibrium of the reaction of the chiral substrate to the factor essential for growth of the cells is shifted in the direction of formation of the factor essential for growth of the cells by addition of an excess amount of the chiral substrate.

6. The method of claim 1, wherein the enantioselective enzyme encoded by a nucleic acid as provided in step (a) is a transaminase.

7. The method of claim 6, wherein the chiral substrate is a specific enantiomer of an amino acid.

8. The method of claim 6, wherein the chiral substrate comprises an α-keto acid.

9. The method of claim 6, wherein the chiral substrate comprises a specific enantiomer of an amino donor.

10. The method of claim 9, wherein the equilibrium of the reaction is shifted in the direction of an amino acid product formation by addition of excess chiral amino donor.

11. The method of claim 10, further comprising adding an α-keto acid amino acceptor to the growth medium.

12. The method of claim 7, wherein the equilibrium of the reaction of the chiral substrate to the factor essential for growth of the cells is shifted in the direction of factor essential for growth of the cells formation by enzymatic removal of an α-keto acid product.

13. The method of claim 7, wherein the equilibrium of the reaction of the chiral substrate to the factor essential for growth of the cells is shifted in the direction of factor essential for growth of the cells formation by chemical removal of an α-keto acid.

14. The method of claim 1, wherein the enzyme is a nitrilase.

15. The method of claim 14, wherein the chiral substrate comprises a specific enantiomer of a nitrile-containing compound.

16. The method of claim 14, wherein the chiral substrate comprises a specific enantiomer of a carboxylic acid.

17. The method of claim 14, wherein the medium comprises a nitrogen-free minimal media for cell growth.

18. The method of claim 1, wherein the enantioselective enzyme encoded by a nucleic acid as provided in step (a) is an aldolase.

19. The method of claim 18, wherein the factor essential for growth of the cells comprises a chiral acetaldehyde.

20. The method of claim 1, wherein the enzyme is an epoxide hydrolase.

21. The method of claim 20, wherein the chiral substrate comprises a chiral epoxide that is hydrolyzed to a diol.

22. The method of claim 20, wherein the chiral substrate comprises a chiral glycidol.

23. The method of claim 20, wherein the chiral substrate comprises a chiral propylene oxide.

24. The method of claim 18, wherein the factor essential for growth of the cells comprises glyceraldehyde-3-phosphate.

25. The method of claim 18, wherein chiral substrate comprises deoxyribose, deoxyribose-5-phosphate, 5-O-methyl-deoxyribose, or dideoxyribose.

26. The method of claim 18, wherein the factor essential for growth of the cells comprises a glyceraldehyde group.

27. The method of claim 18, wherein the chiral substrate comprises a deoxyribose group.

28. The method of claim 18, wherein the factor essential for growth of the cells comprises a lactaldehyde group.

29. The method of claim 1, wherein the nucleic acids of step (a) further comprise or are inserted in a vector, an expression cassette, an expression vector, a phage or a plasmid.

30. The method of claim 29, wherein the vector or expression vector comprises or is a PAC, a BAC, a MAC or a YAC.

31. The method of claim 1, wherein the medium comprises a solid substrate or liquid medium.

32. The method of claim 1, wherein the cells of step (b) are auxotrophs.

33. The method of claim 32, wherein the auxotrophs are amino acid auxotrophs.

34. The method of claim 33, wherein the auxotrophs are manufactured to lack an active form of the enantioselective enzyme by knocking out the gene that encodes the enantioselective enzyme.

35. The method of claim 34, wherein the gene that encodes the enantioselective enzyme is knocked out by transposon mutagenesis.

36. The method of claim 1, wherein step (c) comprises transforming the cells with the nucleic acids of step (a).

37. The method of claim 1, wherein the cells of step (a) comprise bacterial cells.

38. The method of claim 37, wherein the bacterial cells comprise *E. coli, Streptomyces*, or *Bacillus subtilis*.

39. The method of claim 1, wherein the cells of step (a) comprise fungal cells.

40. The method of claim 39, wherein the fungal cells comprise *Aspergillus*.

41. The method of claim 1, wherein the cells of step (a) comprise insect cells.

42. The method of claim 41, wherein the insect cells comprise *Drosophila* S2 or *Spodoptera* Sf9.

43. The method of claim 1, wherein the cells of step (a) comprise animal cells.

44. The method of claim 43, wherein the animal cells comprise a CHO cell, a COS cell or a Bowes melanoma cell.

45. The method of claim 1, wherein the cells of step (a) comprise plant cells.

46. The method of claim 1, wherein the chiral substrate is provided in a single chirality.

47. The method of claim 18, wherein the chiral substrate is a chiral aldolase substrate.

48. The method of claim 18, wherein the aldolase is selected from the group consisting of deoxyribose-5-phosphate (DERA) aldolase, neuraminic acid (NeuAc) aldolase, 6-phosphogluconate (KDPG) aldolase, threonine aldolase, fructose-1,6-diphosphate (FDP) aldolase, hydroxyketomethylglutarate aldolase, and dihydroxyacetone phosphate (DHAP)-dependent aldolase.

49. The method of claim 47, wherein said chiral aldolase substrate comprises a chiral dicarboxylic acid.

50. The method of claim 49, wherein the factor essential for cell growth comprises a keto acid.

51. The method of claim 49, wherein the factor essential for cell growth comprises a pyruvate.

52. The method of claim 51, wherein the enantioselective enzyme is a hydroxyketomethylglutarate aldolase.

53. The method of claim 47, wherein said chiral aldolase substrate comprises a diol phosphate.

54. The method of claim 53, wherein the factor essential for cell growth comprises a chiral aldehyde, a chiral aldehyde phosphate, or both.

55. The method of claim 53, wherein the factor essential for cell growth comprises a chiral acetaldehyde, a chiral glyceraldehyde-3-phosphate, or both.

56. The method of claim 55, wherein the enantioselective enzyme is a deoxyribose-5-phosphate (DERA).

57. The method of claim 47, wherein the factor essential for cell growth comprises a keto acid, an aldehyde, or both.

58. The method of claim 47, wherein the factor essential for cell growth comprises a chiral pyruvate, a chiral compound, or both.

59. The method of claim 58, wherein the enantioselective enzyme is a NeuAc aldolase.

60. The method of claim 47, wherein the factor essential for cell growth comprises a chiral pyruvate, a chiral glyceraldehyde-3-phosphate, or both.

61. The method of claim 60, wherein the enantioselective enzyme is a KDPG aldolase.

62. The method of claim 47, wherein said chiral aldolase substrate comprises a chiral amino acid.

63. The method of claim 62, wherein said chiral amino acid is a threonine.

64. The method of claim 62, wherein the factor essential for cell growth comprises a chiral amino acid, a chiral aldehyde, or both.

65. The method of claim 62, wherein the factor essential for cell growth comprises a chiral amino-acetic acid, a chiral acetaldehyde, or both.

66. The method of claim 65, wherein the enantioselective enzyme is a threonine aldolase.

67. The method of claim 47, wherein said chiral aldolase substrate comprises a chiral deoxyribose-5-phosphate residue.

68. The method of claim 67, wherein the factor essential for cell growth comprises a chiral glyceraldehyde-3-phosphate, chiral aldolase compound, or both.

69. The method of claim 68, wherein the enantioselective enzyme is an FDP aldolase.

70. The method of claim 47, wherein said chiral aldolase substrate comprises a chiral diol phosphate.

71. The method of claim 70, wherein said chiral aldolase substrate comprises a substrate for a DHAP.

72. The method of claim 70, wherein the factor essential for cell growth comprises an aldehyde, DHAP, or both.

73. The method of claim 72, wherein the enantioselective enzyme is a dihydroxy acetone phosphate (DHAP)-dependent aldolase.

74. The method of claim 1, wherein the chiral substrate of step (d) is substantially enantiomerically pure.

75. The method of claim 1, wherein the chiral substrate of step (d) comprises a racemic mixture.

\* \* \* \* \*

SEQUENCE LISTING

```
<160> NUMBER OF SEQ ID NOS: 3

<210> SEQ ID NO 1
<211> LENGTH: 8
<212> TYPE: DNA
<213> ORGANISM: Artificial Sequence
<220> FEATURE:
<223> OTHER INFORMATION: Linker

<400> SEQUENCE: 1 ggaattcc                                                                   8

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agagtttgat cctggctcag                                                     20

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
ggttaccttg ttacgactt                                                      19
```